US006110955A

United States Patent [19]
Nudelman et al.

[11] Patent Number: 6,110,955
[45] Date of Patent: Aug. 29, 2000

[54] METABOLICALLY STABILIZED OXYALKYLENE ESTERS AND USES THEREOF

[75] Inventors: Abraham Nudelman, Rehovot, Israel; Ada Rephaeli, North Caldwell, N.J.; Edward Neiss, New Canaan, Conn.; Bernard Loev, Medford, N.J.

[73] Assignee: Beacon Laboratories, Inc., Phoenix, Md.

[21] Appl. No.: 08/814,975

[22] Filed: Mar. 11, 1997

[51] Int. Cl.[7] ..................... A61K 31/235; A61K 31/407; C07C 69/025; C07D 491/052

[52] U.S. Cl. ..................... 514/411; 424/85.5; 514/12; 514/262; 514/374; 514/413; 514/420; 514/423; 514/532; 514/539; 514/544; 514/545; 548/236; 548/432; 548/453; 548/492; 548/539; 560/10; 560/47; 560/48; 560/52; 560/59; 560/66; 560/70; 560/71; 560/100; 560/102

[58] Field of Search ............... 560/105, 10, 47, 560/48, 52, 59, 66, 70, 71, 100, 102; 514/532, 375, 411, 413, 420, 423, 539, 544, 545; 548/236, 432, 453, 492, 539

[56] References Cited

U.S. PATENT DOCUMENTS

| | | | |
|---|---|---|---|
| 2,940,855 | 6/1960 | Beavers et al. | 96/107 |
| 3,219,630 | 11/1965 | Sidi | 260/67 |
| 3,293,220 | 12/1966 | Minami et al. | 260/67 |
| 3,336,262 | 8/1967 | Sidi | 260/67 |
| 3,578,671 | 5/1971 | Brown . | |
| 3,720,706 | 3/1973 | Lapporte et al. | 260/494 |
| 3,752,844 | 8/1973 | Pfister et al. | 260/470 |
| 3,812,176 | 5/1974 | Lapporte et al. | 260/494 |
| 3,931,412 | 1/1976 | Kensler, Jr. et al. | 424/313 |
| 4,012,526 | 3/1977 | Kensler, Jr. et al. | 424/311 |
| 4,105,681 | 8/1978 | Bollag et al. | 260/404 |
| 4,123,552 | 10/1978 | Kensler, Jr. et al. | 424/311 |
| 4,150,137 | 4/1979 | Noda et al. | 514/345 |
| 4,198,416 | 4/1980 | Koeda et al. | 424/260 |
| 4,215,215 | 7/1980 | Bollag et al. | 547/427 |
| 4,442,124 | 4/1984 | Niklaus | 424/311 |
| 4,541,944 | 9/1985 | Sanderson | 252/95 |
| 4,545,784 | 10/1985 | Sanderson | 8/107 |
| 4,613,505 | 9/1986 | Mizushima et al. | 424/80 |
| 4,699,925 | 10/1987 | Uchida et al. | 514/559 |
| 4,760,057 | 7/1988 | Alexander | 514/187 |
| 4,885,311 | 12/1989 | Parish et al. | 514/549 |
| 4,900,478 | 2/1990 | Gross | 260/408 |
| 4,916,230 | 4/1990 | Alexander | 546/318 |
| 5,025,029 | 6/1991 | Perrine | 514/381 |
| 5,158,773 | 10/1992 | Gross | 424/401 |
| 5,162,573 | 11/1992 | Chiesi et al. | 560/224 |
| 5,185,436 | 2/1993 | Villa et al. | 536/4.1 |
| 5,196,567 | 3/1993 | Uchida et al. | 560/102 |
| 5,200,553 | 4/1993 | Nudelman et al. | 560/263 |
| 5,216,004 | 6/1993 | Perrine | 514/381 |
| 5,569,675 | 10/1996 | Rephaeli et al. | 514/547 |
| 5,661,179 | 8/1997 | Samid | 514/538 |
| 5,710,176 | 1/1998 | Rephaeli et al. | 514/548 |

FOREIGN PATENT DOCUMENTS

| | | |
|---|---|---|
| 890221 | 1/1982 | Belgium . |
| 0 056 189 A1 | 7/1982 | European Pat. Off. . |
| 132 814 | 2/1985 | European Pat. Off. . |
| 144 845 | 6/1985 | European Pat. Off. . |
| 250 967 A2 | 1/1988 | European Pat. Off. . |
| 0 371 789 A2 | 6/1990 | European Pat. Off. . |
| 1386096 | of 1965 | France . |
| 1540418 | 9/1968 | France . |
| 54-90174 | 7/1979 | Japan . |
| 58-15912 | 1/1983 | Japan . |
| 60-016923 | 1/1985 | Japan . |
| 63-101348 | 5/1988 | Japan . |
| 635 062 | 3/1983 | Switzerland . |
| 1177442 | 1/1970 | United Kingdom . |
| 1 220 442 | 1/1971 | United Kingdom . |
| 1 220 447 | 1/1971 | United Kingdom . |
| 1 345 628 | 1/1974 | United Kingdom . |
| 1 382 010 | 1/1975 | United Kingdom . |
| 2126082 | 3/1984 | United Kingdom . |
| WO93/07866 | 4/1993 | WIPO . |
| WO93/19778 | 10/1993 | WIPO . |
| WO95/10271 | 4/1995 | WIPO . |

OTHER PUBLICATIONS

Bhatia, et al., "Induction of Cell Differentiation Potentiates Apoptosis by Sodium Triggered by Prior Exposure to DNA–damaging Drugs", Cell Growth and Differentiation, vol. 6, pp. 937–944, 1995.

Boffa, et al., "Manifold Effects of Sodium Butyrate on Nuclear Function", J. Biol. Chem., vol. 256, No. 18, pp. 9612–9621, 1981.

Bourgeade, et al., "Reorganization of the Cytoskeleton by Interferon in MSV–Transformed Cells", J. of Interferon Res., vol. 1, No. 2, pp. 323–332, 1981.

Brant and Conklin, "Acrolein Diacylates", Chem. Abstracts, vol. 40, p. 3127, 1946.

Carstea, et al., "Analogues of Butyric Acid that Increase the Expression of Transfected DNAs", Biochem. Biophys. Res. Com., vol. 192, No. 2, pp. 649–656, 1993.

Cheng, et al., "Functional Activation of the Cystic Fibrosis Trafficking Mutant deltaF508–CFTR by Overexpression", American Journal of Physiology, vol. 268, No. 4, pp. L615–L624, 1995.

(List continued on next page.)

*Primary Examiner*—Richard L. Raymond
*Attorney, Agent, or Firm*—Kenyon & Kenyon

[57] ABSTRACT

This invention relates to compositions for and methods of treating, preventing or ameliorating cancer and other proliferative diseases as well as methods of inducing wound healing, treating cutaneous ulcers, treating gastrointestinal disorders, treating blood disorders such as anemias, immunomodulation, enhancing recombinant gene expression, treating insulin-dependent patients, treating cystic fibrosis patients, inhibiting telomerase activity, treating virus-associated tumors, especially EBV-associated tumors, modulating gene expression and particularly augmenting expression of a tumor suppressor gene, inducing tolerance to an antigen and treating, ameliorating or preventing protozoan infection. The methods of the invention use metabolically stabilized oxyalkylene esters.

50 Claims, 5 Drawing Sheets

OTHER PUBLICATIONS

Conway, et al., "Induction of Apoptosis by Sodium Butyrate in the Human Y–79 Retinoblastoma Cell Line", Oncology Research, vol. 7, No. 6, pp. 289–297, 1995.

de Haan, et al., "Effects of Sodium Butyrate on the Synthesis and Methylation of DNA in Normal Cells and Their Transformed Counterparts", Cancer Res., vol. 46, No. 2, pp. 713–716, 1986.

Deschamps, et al., "Inhibition by Salicylic Acid of the Activation and Thus Oxidation of Long Chain Fatty Acids. Possible Role in the Development of Reye's Syndrome", J. Pharm. Exp. Ther., vol. 259, No. 2, pp. 894–904, 1991.

Fishman and Atikkan, "Induction of Cholera Toxin Receptors in Cultured Cells by Butyric Acid", J. Biol. Chem., vol. 254, No. 11, pp. 4342–4344, 1979.

Freneaux, et al., "Inhibition of the Mitochondrial Oxidation of Fatty Acids by Tetracycline in Mice and in Man: Possible Role in Microvesicular Steatosis Induced by This Antibiotic", Hepatology, vol. 8, No. 5, pp. 1056–1062, 1988.

Freneaux, et al., "Stereoselective and Nonstereoselective Effects of Ibuprofen Enantiomers on Mitochondrial beta–Oxidation of Fatty Acids", J. Pharm Exp.Ther., vol. 255, No. 2, pp. 529–535, 1990.

Fromenty, et al., "Tianeptine a New Tricyclic Antidepressant Metabolized by beta–Oxidation of its Hepatanoic Side Chain, Inhibits the Mitochondrial Oxidation of Medium and Short Chain Fatty Acids in Mice", Biochem. Pharm., vol. 38, No.21, pp. 3743–3751, 1989.

Fromenty, et al., "Dual Effect of Amiodarone on Mitochondrial Respiration. Initial Protonophoric Uncoupling Effect Followed by Inhibition of the Respiratory Chain at the Levels of Complex I and Complex II", J. Pharm. Exp. Ther., vol. 255, No. 3, pp. 1377–1384, 1990.

Hague, et al., "Apoptosis in Colorectal Tumor Cells: Induction by the Short Chain Fatty Acids Butyrate, Propionate and Acetate and by the Bile Salt Deoxycholate", Int. J. Cancer, vol. 60, pp. 400–406, 1995.

Ingram and Thomas, "The Electron Impact Inducd Fragmentation of Geminal Dialkanoates", Organic Mass Spectrometry, vol. 12, No. 4, pp. 216–221, 1977.

Le Dinh, et al., "Amineptine, a Tricyclic Antidepressant, Inhibits the Mitochondrial Oxidation of Fatty Acids and Produces Microvesicular Steatosis of the Liver in Mice", J. Pharm. Exp. Ther., vol. 247, No. 2, pp. 745–750, 1988.

Loftsson and Bodor, "Improved Delivery through Biological Membranes IX: Kinetics and Mechanism of Hydrolysis of Methylsulfinylmethyl 2–Acetoxybenzoate and Related Aspirin Prodrugs", J. Pharm. Sci., vol. 70, No. 7, pp. 750–755, 1981.

Los, et al., "Synthesis of Some New Derivatives of 2–Hydroxy and 2–Acetyloxybenzoic Acids", Boll. Chim. Farm., vol. 121, pp. 285–302, 1982.

Man, et al., "Boron Fluoride Catalyzed Addition of Aliphatic Anhydrides to Aldehydes", J. Am. Chem. Soc., pp. 847–848, 1950.

Miller, et al., "Clinical Pharmacology of Sodium Butyrate in Patients with Acute Leukemia", Eur. J. Cancer Clin Oncol. vol. 23, No. 9, pp. 1283–1287, 1987.

Mosher and Kehr, "The Oxidation of Aliphatic Esters with Lead Tetraacetate", J. Am. Chem. Soc., vol. 82, pp. 5342–5345, 1960.

Nielsen and Bundgaard, "Evaluation of Glycolamide Esters and Various Other Esters of Aspirin as True Aspirin Prodrugs", J. Medicinal Chem., vol. 32, pp. 727–734, 1989.

Nordenberg, et al., "Growth Inhibition of Murine Melanoma by Butyric Acid and Dimethylsulfoxide", Exp. Cell Res., vol. 162, pp. 77–85, 1986.

Nordenberg, et al., "Biochemical and Ultrastructural Alterations Accompany the Anti–proliferative Effect of Butyrate on Melanoma Cells", Br. J. Cancer, vol. 55, pp. 493–497, 1987.

Novogrodsky, et al., "Effect of Polar Organic Compounds on Leukemic Cells", Cancer, vol. 51, No. 1, pp. 9–14, 1983.

Nudelman, et al., "Novel Anticancer Prodrugs of Butyric Acid", J. Med. Chem., vol. 35, pp. 687–694, 1992.

Oh, et al., "Convenient Synthesis of Geminal Biscarboxylates:Searching for an Efficient Route to HR 916B", Korean J. Med. Chem., vol. 6, No. 2, pp. 259–262, 1996.

Prasad, "Butyric Acid: A Small Fatty Acid with Diverse Biological Functions", Life Sci., vol. 27, No. 15, pp. 1351–1358, 1980.

Prasad, et al., "Decreased Expressions of c–myc and H–ras Oncogenes in Vitamin E Succinate Induced Morphologically Differentiated Murine B–16 Melanoma Cells in Culture", Biochem. Cell Bio., vol. 68, No. 11, pp. 1250–1255, 1990.

Rabizadeh, et al., "Rapid Alteration of c–myc and c–jun Expression in Leukemic Cells Induced to Differentiate By a Butyric Acid Prodrug", FEBS Lett., vol. 328, No. 3, pp. 225–229, 1993.

Ramain, et al.,"Amineptine Hepatitis: Report of Two Cases", Gastroenterol. Clin. Biol., vol. 5, pp. 469–471, 1981.

Rephaeli, et al., "Butyrate–Induced Differentiation in Leukemic Myeloid Cells: in vitro and in vivo Studies", International Journal of Oncology, vol. 4, No. 6, pp. 1387–1391, 1994.

Riggs, et al., "n–Butyrate Causes Histone Modification in HeLa and Friend Erythroleukaemia Cells", Nature, vol. 268, No.5617, pp. 462–464, 1977.

Roedinger and Millard, "Selective Inhibition of Fatty Acid Oxidation in Colonocytes by Ibuprofen: A Cause of Colitis?", Gut, vol. 36, pp. 55–59, 1995.

Rottleb, et al., "Structure–Activity Relationship of 17 Structural Analogues of N–Butyric Acid Upon c–myc Expression", Int. J. Cancer, vol. 67, pp. 724–729, 1996.

Samid, et al., "Phenylacetate: A Novel Nontoxic Inducer of Tumor Cell Differentiation", Cancer Res., vol., 52, No. 7, pp. 1988–1992, 1992.

Sanderson, et al., "Bleach Compositions", Chem. Abstracts, vol.102, Abstract 47772t, 1985.

Sher, et al., "Extended Therapy with Intravenous Arginine Butyrate in Patients with Beta–Hemoglobinopathies", New England Journal Medicine, vol. 332, No. 24, pp. 1606–1610, 1995.

Smigel, "Nontoxic Drug Being Tested to Treat Cancer and Anemias", J. Nat'l Cancer Inst., vol. 84, No.18, pp. 1398–1399, 1992.

Smith, et al., "Incorporation of Tributyrin Enhances the Expression of a Reporter Gene in Primary and Immortalized Cell Lines", Biotechniques, vol. 18, No. 5, pp. 852–855, 1995.

Stamatoyannopoulos, et al., "Therapeutic Approaches to Hemoglobin Switching in Treatment of Hemoglobinopathies", Ann. Rev. Med., vol. 43, pp. 497–522, 1992.

Tang, et al., "Butyrate–Inducible and Tumor–Restricted Gene Expression by Adenovirus Vectors", Cancer Gene Therapy, vol. 1, No. 1, pp. 15–20, 1994.

Thorne, et al., "Patterns of Histone Acetylation", Eur. J. Biochem., vol. 193, pp. 701–713, 1990.

Tomiska and Spousta, "Low–Molecular Polyoxymethylene Diacetates from Trioxane", Angew. Chem. Internat. Edit., vol. 1, No. 4, p 211, 1962.

Toscani, et al., "Molecular Analysis of Sodium Butyrate–Induced Growth Arrest", Oncogene Res., vol. 3, No. 3, pp. 223–238, 1988.

Toyobo Co., "Electroconductive Resin Compositions", Chem. Abstracts, vol. 103, Abstract 125229h, 1985.

Vernia, et al., "Topical Treatment of Refractory Distal Ulcerative Colitis with 5–ASA and Sodium Butyrate", Digestive Diseases and Sciences, vol. 40, No. 2, pp. 305–307, Feb. 1995.

METABOLICALLY STABILIZED OXYALKYLENE ESTERS AND USES THEREOF

FIELD OF THE INVENTION

This invention relates to compounds and compositions for and methods of treating, preventing or ameliorating cancer and other proliferative diseases as well as methods of inducing wound healing, treating cutaneous ulcers, treating gastrointestinal disorders, treating blood disorders such as anemias, immunomodulation, enhancing recombinant gene expression, treating insulin-dependent patients, treating cystic fibrosis patients, inhibiting telomerase activity, treating virus-associated tumors, especially EBV-associated tumors, modulating gene expression and particularly augmenting expression of tumor suppressor genes, inducing tolerance to antigens, reducing pain and/or inflammation and treating, ameliorating or preventing protozoan infection and inhibiting histone deacetylase in cells. The methods of the invention use oxyalkylene butyrate esters.

BACKGROUND OF THE INVENTION

Butyric acid (BA) is a natural product. It is supplied to mammals from two main sources: 1) the diet, mainly from dairy fat, and 2) from the bacterial fermentation of unabsorbed carbohydrates in the colon, where it reaches mM concentrations (Cummings, *Gut* 22:763–779,1982; Leder et al., *Cell* 5:319–322, 1975).

BA has been known for nearly the last three decades to be a potent differentiating and antiproliferative agent in a wide spectrum of neoplastic cells in vitro (Prasad, *Life Sci.* 27:1351–1358, 1980). In cancer cells, BA has been reported to induce cellular and biochemical changes, e.g., in cell morphology, enzyme activity, receptor expression and cell-surface antigens (Nordenberg etal., *Exp. Cell Res.* 162:77–85, 1986; Nordenberg et al., *Br. J. Cancer* 56:493–497, 1987; and Fishman et al., *J. Biol. Chem.* 254:4342–4344, 1979).

Although BA or its sodium salt (sodium butyrate, SB) has been the subject of numerous studies, its mode of action is unclear. The most specific effect of butyric acid is inhibition of nuclear deacetylase(s), resulting in hyperacetylation of histones H3 and H4 (Riggs, et al., *Nature* 263:462–464, 1977). Increased histone acetylation following treatment with BA has been correlated with changes in transcriptional activity and the differentiated state of cells (Thorne et al., *Eur. J. Biochem.* 193:701–713, 1990). BA also exerts other nuclear actions, including modifications in the extent of phosphorylation (Boffa et al., *J. Biol. Chem.* 256:9612–9621, 1981) and methylation (Haan et al., *Cancer Res.* 46:713–716, 1986). Other cellular organelles, e.g., cytoskeleton and membrane composition and function, have been shown to be affected by BA (Bourgeade et al., *J. Interferon Res.* 1:323–332, 1981). Modulations in the expression of oncogenes and suppressor genes by BA were demonstrated in several cell types. Toscani et al., reported alterations in c-myc, p53 thymidine kinase, c-fos and AP2 in 3T3 fibroblasts (*Oncogene Res.* 3:223–238, 1988). A decrease in the expression of c-myc and H-ras oncogenes in B16 melanoma and in c-myc in HL60 promyelocytic leukemia was also reported (Prasad et al., *Biochem. Cell Biol.* 68:1250–1255, 1992: and Rabizadeh et al., *FEBS Lett.* 328:225–229, 1993).

BA has been reported to induce apoptosis, i.e., programmed cell death. SB has been shown to produce apoptosis in vitro in human colon carcinoma, leukemia and retinoblastoma cell lines (Bhatia et al., *Cell Growth Diff.* 6:937–944, 1995; Conway et al., *Oncol. Res.* 7:289–297, 1993; Hague et al.; *Int. J. Cancer* 60:400–406, 1995). Apoptosis is the physiological mechanism for the elimination of cells in a controlled and timely manner. Organisms maintain a delicate balance between cell proliferation and cell death, which when disrupted can tip the balance between cancer, in the case of over accumulation of cells, and degenerative diseases, in the case of premature cell losses. Hence, inhibition of apoptosis can contribute to tumor growth and promote progression of neoplastic conditions.

The promising in vitro antitumor effects of BA and BA salts led to the initiation of clinical trials for the treatment of cancer patients with observed minimal or transient efficacy. [Novogrodsky et al., *Cancer* 51:9–14, 1983; Rephaeli et al., *Intl. J. Oncol.* 4:1387–1391,1994; Miller et al., *Eur. J. Cancer Clin. Oncol.* 23:1283–1287,1987].

Clinical trials have been conducted for the treatment of β-globin disorders (e.g., β-thalassemia and sickle-cell anemia) using BA salts. The BA salts elevated expression of fetal hemoglobin (HbF), normally repressed in adults, and favorably modified the disease symptoms in these patients (Stamatoyannopouos et al., *Ann. Rev. Med.* 43:497–521, 1992). In this regard, arginine butyrate (AB) has been used in clinical trials with moderate efficacy (Perrine et al., *N. Eng. J. Med.* 328:81–86, 1993; Sher et al., *N. Eng. J. Med.* 332:1606–1610, 1995). The reported side effects of AB included hypokalemia, headache, nausea and vomiting in β-thalassemia and sickle-cell anemia patients.

Butyric acid derivatives having antitumor activity and immunomodulatory properties have been reported in U.S. Pat. No. 5,200,553 and by Nudelman et al., 1992, *J. Med. Chem.* 35:687–694. The most active butyric acid prodrug reported in these references was pivaloyloxymethyl butyrate. None of the compounds disclosed in these references included oxyalkylene butyrate compounds of this invention.

BA and/or its analogues have also been reported to increase the expression of transfected DNA (Carstea et al., 1993, *Biophys. Biohem. Res. Comm.* 192:649; Cheng et al., 1995,*Am. J. Physical* 268:L615–L624) and to induce tumor-restricted gene expression by adenovirus vectors (Tang et al., 1994, *Cancer Gene Therapy* 1:15–20). Tributyrin has been reported to enhance the expression of a reporter gene in primary and immortalized cell lines (Smith et al., 1995, *Biotechniques* 18:852–835).

Straight short chain fatty acids such as butyric acid are metabolized by β-oxidation that occurs in the mitochondria. Two-carbon fragments are sequentially removed from the carboxyl end of the fatty acid following dehydrogenation, hydration and oxidation to form a β-keto acid, which is then split by thiolysis. Consequently, BA and its salts are normally metabolized rapidly and have very short half-lives in vivo, such that the achievement and maintenance of effective plasma concentrations are problems associated with BA and BA salts, particularly for in vivo uses. BA and BA salts have required large doses to achieve even minimal therapeutic effects. Because of the high dosage, fluid overload and mild alkalosis may occur. Patients receiving BA emanate an unpleasant odor that is socially unacceptable.

Several drugs have been shown to decrease mitochondrial β-oxidation of fatty acids, such as ibuprofen (Freneaux, et al., 1990, *J. Pharmacol. Exp. Ther.*, 255:529–535), aminetepine (Ramain, et al., 1981, Gastroenterol. Clin. Biol., 5:469471; Le Dinh, et al., 1988, J. Pharmacol. Exp.

Ther., 247:745–750), tianeptine (Fromenty, et al., 1989, Biochem. Pharmacol., 38:3743–3751), aminodarone (Fromenty, et al., 1990, Biochem. Pharmacol., 255:1377–1384), tetracycline (Zimmerman, et al., 1988, Hepatology, 8:1056–1062), and valproic acid and salicylic acid (Deschamps, et al., 1991, J. Pharmacol. Exp. Ther., 259:894–904).

While BA salts have been shown to increase HbF expression, and appear to hold therapeutic promise with low toxicity in cancer patients, they nevertheless have shown low potency in in vitro assays and clinical trials. There also remains a need to identify compounds as effective or more effective than BA or BA salts as differentiating or anti-proliferating agents for the treatment of cancers. Such compounds need to have higher potency than BA without the problems associated with BA (such as bad odor). Consequently, there remains a need for therapeutic compounds that either deliver BA to cells in a longer acting form or which have similar activity as BA but a longer duration of effectiveness in vivo.

The compounds of this invention address these needs and are more potent than BA or BA salts for treating cancers and other proliferative diseases, for treating gastrointestinal disorders, for wound healing and for treating blood disorders such as thalassemia, sickle cell anemia and other anemias, for modulating an immune response, for enhancing recombinant gene expression, for treating insulin-dependent patients, for treating cystic fibrosis patients, for inhibiting telomerase activity, for detecting cancerous or malignant cells, for treating virus-associated tumors, especially EBV-associated tumors, for modulating gene expression and particularly for augmenting expression of a tumor suppressor gene, for inducing tolerance to an antigen, reducing pain and/or inflammation for treating preventing or amelioraating protozoan infection and for inhibiting histone deactylase in cells. One of the advantages of the compounds of the invention is increased water solubility of the free carboxylic acids compounds of the invention and their salts, and easier administration, especially for intravenous administration.

SUMMARY OF THE INVENTION

Accordingly, one embodiment of the present invention is directed to a method of treating, preventing or ameliorating cancer and other proliferative disorders using compounds represented by Formula (I):

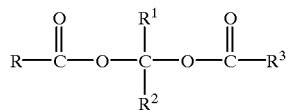

(I)

wherein

R is a $C_1$ to $C_{10}$ alkyl, $C_2$ to $C_{10}$ alkenyl, or $C_2$ to $C_{10}$ alkynyl group optionally substituted with an alkoxy, halo, trifluoromethyl, amino, acylamino, hydroxy, carbonyl, aryl, substituted aryl, heteroaryl or substituted heteroaryl group;

$R^1$ and $R^2$ are each independently H, $C_1$ to $C_6$ straight or branched chain alkyl, $C_2$ to $C_6$ branched or straight chain alkenyl or $C_2$ to $C_6$ branched or straight chain alkynyl, wherein the alkyl, alkenyl or alykynyl group or a combination thereof is optionally substituted with halo or alkoxy; and $R^3CO$ is an acyl moiety of a carboxylic acid-containing compound that inhibits beta-oxidation of fatty acids;

or a pharmaceutically acceptable salt thereof.

In a preferred embodiment, the acyl moiety of the compound is the acyl moiety of a non-steroidal anti-inflammatory drug (NSAID). In another preferred embodiment, $R^2$ is hydrogen.

The methods of the present invention are particularly useful for treating, preventing or ameliorating the effects of cancer or other proliferative disorders by acting as an anti-proliferative or differentiating agent in subjectsd afflicted with such anomalies. Such disorders include but are not limited to leukemias, such as acute promyelocytic leukemia, acute myeloid leukemia, and acute myelomonocytic leukemia; other myelodysplastic syndromes, multiple myeloma such as but not limited to breast carcinomas, cervical cancers, melanomas, colon cancers, nasopharyngeal carcinoma, non-Hodgkins lymphoma (NHL), Kaposi's sarcoma, ovarian cancers, pancreatic cancers, hepatocarcinomas, prostate cancers, squamous carcinomas, other dermatologic malignancies, teratocarcinomas, Tcell lymphomas, lung tumor, gliomas, neuroblastomas, peripheral neuroectodermal tumors, rhabdomyosarcomas, and prostate tumors and other solid tumors. It is also possible that compounds of Formula (I) have anti-proliferative effects on non-cancerous cells as well, and may be of use to treat benign tumors and other proliferative disorders such as psoriasis. Preferred is the method for treating or ameliorating leukemia, squamous cell carcinoma and neuroblastoma.

Another embodiment of the present invention is directed to methods of treating, preventing or ameliorating cancer and other proliferative disorders by administering a therapeutically effective amount of a compound of Formula (I) to a subject suffering from such disorders together with a pharmaceutical agent (e.g., a known antiproliferative, differentiating or oncostatic agent) to thereby enhance the action of these agents. Such agents include but are not limited to, cytokines, interleukins, anti-cancer agents, chemotherapeutic agents, antibodies, conjugated antibodies, immune stimulants, antibiotics, hormone antagonists, and growth stimulants. The compounds of the invention can be administered prior to, after or concurrently with any of the agents.

Yet another embodiment of the invention is directed to a method of ameliorating the effects of a cytotoxic agent which comprises administering a therapeutically-effective amount of a cytotoxic agent with a compound of Formula (I) to a mammalian patient for a time and in an amount to induce growth arrest of rapidly-proliferating epithelial cells of the patient and thereby protect those cells from the cytotoxic effects of the agent. The cytotoxic agent can be a chemotherapeutic agent, an anticancer agent, or radiation therapy, for example. Rapidly proliferating epithelial cells are found in hair follicles, the gastro-intestinal tract, the bladder and bone marrow, for example. Such cells include hair follicle cells, or intestinal cryt cells. Rapidly proliferating cells are also found in the bone marrow and include bone marrow stem cells. In accordance with the invention the cytotoxic agent and the compound of Formula I can be administered simultaneously, or the cytotoxic agent can be administered prior to or after the compound of the invention. Administration (simultaneously or at a different time) can be done systemically or topically as determined by the indication. In addition, when the cytotoxic agent is radiation therapy, the compounds of the invention can be administered to a cancer patient pre- or post-radiation therapy to treat or ameliorate the effects of cancer.

A still further embodiment of the invention is directed to a method of inducing wound healing, treating cutaneous ulcers or treating a gastrointestinal disorder by administering a therapeutically-effective amount of a compound of Formula (I) to a subject in need of such treatment. The cutaneous ulcers which can be treated in accordance with the methods of the invention include leg and decubitus ulcers, stasis ulcers, diabetic ulcers and atherosclerotic ulcers. With respect to wound healing, the compounds are useful in treating abrasions, incisions, burns, and other wounds. Gastrointestinal disorders treatable by the methods of the invention include colitis, inflammatory bowel disease, Crohn's disease and ulcerative colitis.

The invention is further directed to a method of treating blood disorders by administering a therapeutically-effective amount of a compound of Formula (I) to a patient. The blood disorders treatable in accordance with the invention include, but are not limited to, thalassemias, sickle cell anemias, infectious anemias, aplastic anemias, hypoplastic and hypoproliferafive anemias, sideroblastic anemias, myelophthisic anemias, antibody-mediated anemias, anemias due to chronic diseases and enzyme-deficiencies, and anemias due to blood loss, radiation therapy and chemotherapy. In this regard, these methods can include increasing hemoglobin content in blood by administering a therapeutically-effective amount of a compound of Formula (I) to a subject.

Another embodiment of the invention is directed to a method of modulating an immune response in a host by administering an amount of a compound of Formula (I) effective to modulate said immune response. Modulation of the immune response includes enhancing cytokine secretion, inhibiting or delaying apoptosis in polymorphonuclear cells, enhancing polymorphonuclear cell function by augmenting hematopoietic growth factor secretion, inducing expression of cell surface antigens in tumor cells, and enhancing progenitor cell recovery after bone marrow transplantation.

A further embodiment of the invention relates to a method of enhancing recombinant gene expression by treating a recombinant host cell containing an expression system for a mammalian gene product of interest with an expression-enhancing amount of a compound of Formula (I), wherein said gene product is encoded by a butyric acid-responsive gene. The host cells can be mammalian cells, insect cells, yeast cells or bacterial cells and the correspondingly known expression systems for each of these host cells. The gene product can be any protein or peptide of interest expression of which can be regulated or altered by butyric acid or a butyric acid salt. A butylric acid-responsive gene is a gene that has a promoter, enhancer element or other regulon that modulates expression of the gene under its control in response to butyric acid or a salt of butyric acid. For example, gene products contemplated for regulation in accordance with the invention include but are not limited to tumor suppressor genes (such as p53) and the γ-globin chain of fetal hemoglobin.

Yet a further embodiment of the invention is directed to a method of treating, preventing or ameliorating symptoms in insulin-dependent patients by administering an amount of a compound of Formula (I) effective to enhance insulin expression.

Yet another embodiment of the invention relates to a method of treating, preventing or ameliorating symptoms in cystic fibrosis patients by administering an amount of a compound of Formula (I) effective to enhance chloride channel expression.

Still another method of the invention is directed to a method of inhibiting telomerase activity in cancer cells by administering a telomerase-inhibiting amount of a compound of Formula (I) to the cells, wherein the amount is effective to decrease the telomerase activity of the cells and thereby inhibit the malignant progression of the cells. This method can be applied to in vivo or in vitro cells.

Another embodiment of this invention is directed to a method of treating, preventing or ameliorating virus-associated tumors by pre-, post or co-administering a therapeutically-effective amount of a compound of Formula (I) with a therapeutically-effective amount of an antiviral agent. Antiviral agents contemplated for use in the invention include ganciclovir, acyclovir arnd famciclovir, and preferably ganciclovir. The virus-associated tumors which call be treated, prevented or ameliorated in accordance with the invention include but are not limited to, EBV-associated malignancy, Kaposi's sarcoma, AIDS-related lymphoma, hepatitis B-associated malignancy or hepatitis C associated malignancy. EBV-associated malignancies include nasopharyngeal carcinoma and non-Hodgkins' lymphoma and are preferred embodiments of the invention.

Further still, the invention provides a method of modulating gene expression by treating a host or host cells with a compound of Formula I in an amount effective to enhance, augment or repress the expression of a gene of interest, preferably a butyric-acid responsive gene. When expression of the gene of interst is to be enhanced or augmented the gene may encode a gene product which is, for example, a tumor suppressor, or which is or acts as a repressor of another gene, an inducer of apoptosis or an inducer of differentiation. When expression of the gene of interest is to be repressed the gene may encode a gene product which, for example, is or acts as an oncogene or an inhibitior of apoptosis such as, the bcl-2 gene, which encodes an inhibitor of apoptosis.

More particularly, the invention is directed to a method of augmenting gene expression, especially of a tumor suppressor gene, a butyric acid-responsive gene or a fetal hemoglobin gene, by treating a host or host cells with an expression-enhancing amount of a compound of Formula (I). Preferably the host is a cancer patient. This method of the invention thus includes augmenting tumor suppressor gene expression in conjunction with ex vivo or in vivo gene therapy, i.e., the compound of the invention can be co-administered to the host during administration of gene therapy vectors or administration of the ex vivo transfected cells. Similarly, the compounds of the invention can be used to treat cells during the transfection step of ex vivo gene therapy. The hosts of the method therefore include cancer patients or other patients undergoing gene therapy. The host cells of the invention include hematopoietic cells such as stem cells and progenitor cells, e.g., or any other cell type used in ex vivo gene therapy.

Yet another embodiment of the invention is directed to a method of inducing tolerance to an antigen which comprises administering a therapeutically-effective amount of compound of Formula (I). Preferably the antigen is a self-antigen.

Another embodiment of the invention is a method for treating, ameliorating or preventing protozoan infection in a patient comprising administering to the patient an effective amount of a compound of the invention. Protoazoan infections treatable by the method of the invention include, but are not limited to malaria, cryptosporidiosis, taxoplasmosis and coccidiosis.

A further embodiment of the invention is a method for inhibiting historne deacetylase in cells, which comprises administering to the cells an effective amount of a compound of the invention.

A further embodiment of the present invention is directed to pharmaceutical compositions comprising a therapeutically-effective amount of a compound of Formula (I), a pharmaceutical agent and a pharmaceutically-effective carrier or diluent. The pharmaceutical agents of the invention include but are not limited to cytokines, interleukins, anti-ncer agents, chemotherapeutic agents, antibodies, conjugated antibodies, immune stimulants, antibiotics, hormone antagonists or growth stimulants.

In another embodiment of the invention, there is provided a method for treating or preventing pain, fever or inflammation which comprises administering to a patient in need of such treatment a pharmaceutical composition comprising a therapeutically effective amount of a compound having the structural formula (I):

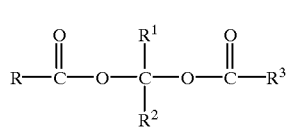

(I)

wherein

R is a $C_1$ to $C_{10}$ alkyl, $C_2$ to $C_{10}$ alkenyl or $C_2$ to $C_{10}$ alkynyl group, optionally substituted with an alkoxy, halo, trifluoromethyl, amino, acylamino, carboxyl, carboxamide, carbalkoxy, hydroxy, carbonyl, aryl, substituted aryl, heteroaryl or substituted heteroaryl group;

$R^1$ and $R^2$ are each independently H, $C_1$ to $C_6$ straight or branched chain alkyl, $C_2$ to $C_6$ branched or straight chain alkenyl or $C_2$ to $C_6$ branched or straight chain alkynyl wherein the alkyl, alkenyl or alkynyl group or a combination thereof is optionally substituted with halo or alkoxy; and $R^3CO$ is an acyl moiety of a carboxylic acid-containing compound thait inhibits beta-oxidation of fatty acids;

with the proviso that when said acyl moiety is the acyl moiety of a NSAID compound, the NSAID is selected from the group consisting of ketoprofen, diflunisal, salsalate, etodolac, tolmetin, ibuprofen, naproxen, oxaprozin, salicylic acid, acetylsalicylic acid, indomethacin, flurbiprofen, diclofenac, mefanamic acid, meclofenamic acid, ketorolac and sulindac; and wherein when the acyl moiety is that of ibuprofen, R is not methyl or ethyl; when the acyl moiety is that of oxaprozin, R is not methyl; when the acyl moiety is that of sulindac or naproxen, R is not alkyl; when the acyl moiety is that of salicylic acid or acetylsalicylic acid, R is $C_3$ to $C_{10}$ alkenyl or lower haloalkyl; and when the acyl moiety is that of indomethacin, flurbiprofen or diclofenac, R is $C_3$ to $C_{10}$ haloalkyl;

or a pharmaceutically acceptable salt thereof.

In another aspect of the invention there is provided a pharmaceutical composition comprising a therapeutically effective amount of a compound of Formula (I).

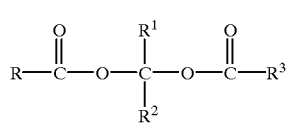

(I)

wherein R is a $C_1$ to $C_{10}$ alkyl, $C_2$ to $C_{10}$ alkenyl or $C_2$ to $C_{10}$ alkynyl group, optionally substituted with an alkoxy, halo, trifluoromethyl, amino, acylamino, carboxyl, carboxamide, carbalkoxy, hydroxy, carbonyl, aryl, substituted aryl, heteroaryl or substituted heteroaryl group;

$R^1$ and $R^2$ are each independently H, $C_1$ to $C_6$ straight or branched chain alkyl, $C_2$ to $C_6$ branched or straight chain alkenyl or $C_2$ to $C_6$ branched or straight chain alkynyl wherein the alkyl, alkenyl or alkynyl group is optionally substituted with halo or alkoxy; and $R^3CO$ is an acyl moiety of a carboxylic acid-containing compound that inhibits beta-oxidation of fatty acids;

with the proviso that when said acyl moiety is the acyl moiety of a NSAID compound, the NSAID is selected from the group consisting of ketoprofen, diflunisal, salsalate, etodolac, tolmetin, ibuprofen, naproxen, oxaprozin, salicylic acid, acetylsalicylic acid, indomethacin, flurbiprofen, diclofenac, mefanamic acid, meclofenamic acid, ketorolac and sulindac; and wherein when the acyl moiety is that of ibuprofen, R is not methyl or ethyl; when the acyl moiety is that of oxaprozin, R is not methyl; when the acyl moiety is that of sulindac or naproxen, R is not alkyl; when the acyl moiety is that of salicylic acid or acetylsalicylic acid, R is $C_3$ to $C_{10}$ alkenyl or lower haloalkyl; when the acyl moiety is that of indomethacin, flurbiprofen or diclofenac, R is $C_3$ to $C_{10}$ haloalkyl; and when the acyl moiety is that of valproic acid or 2-valproenoic acid, R is not $C_1$ to $C_{10}$ alkyl, hydroxypropyl or $C_2$ to $C_{10}$ alkenyl substituted with an aryl group;

or a pharmaceutically acceptable salt thereof.

In another aspect of the invention there is provided a compound having the structural formula (I):

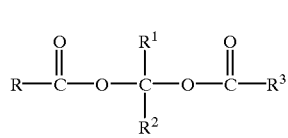

(I)

wherein

R is a $C_1$ to $C_{10}$ alkyl or $C_2$ to $C_{10}$ alkenyl group, optionally substituted with up to two alkyl groups or with an alkoxy, halo, trifluoromethyl, amino, hydroxy, carbonyl, aryl, substituted aryl, heteroaryl or substituted heteroaryl group;

$R^1$ and $R^2$ are each independently H, $C_1$ to $C_6$ straight or branched chain alkyl or $C_2$ to $C_6$ branched or straight chain alkenyl; and $R^3CO$ is an acyl moiety of a carboxylic acid-containing compound that inhibits beta-oxidation of fatty acids;

with the proviso that when said acyl moiety is the acyl moiety of a NSAID, the NSAID is selected from the group consisting of ketoprofen, diflunisal, salsalate, etodolac, tolmetin, ibuprofen, naproxen, oxaprozin, salicylic acid, acetylsalicylic acid, indomethacin, flurbiprofen, diclofenac, mefanamic acid, meclofenamic acid ketorolac and sulindac; and wherein when the acyl moiety is that of ibuprofen, R is not methyl or ethyl; when the acyl moiety is that of oxaprozin, R is not methyl; when the acyl moiety is that of sulindac or naproxen, R is not alkyl; when the acyl moiety is that of salicylic acid or acetylsalicylic acid, R is $C_3$ to $C_{10}$ alkenyl or lower haloalkeny; when the acyl moiety is that of indomethacin, flurbiprofen or diclofenac, R is $C_3$ to $C_{10}$ haloalkyl; and when the acyl moiety is that of valproic acid or 2-valproenoic acid, R is not $C_1$ to $C_{10}$ alkyl, hydroxy propyl or $C_2$ to $C_{10}$ alkenyl substituted with an aryl group;

or a pharmaceutically acceptable salt thereof.

In a preferred embodiment, $R^2$ of the compounds of the invention is hydrogen.

DETAILED DESCRIPTION OF THE INVENTION

Figure 1A:
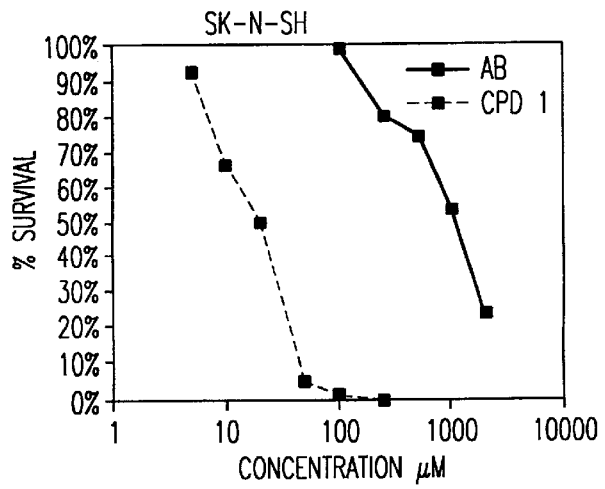
FIGS. 1A–1C are graphic illustrations showing the in vitro inhibition of cellular growth (clonogenicity) by α-methyl-4-(2-methylpropyl)-benzeneacetyloxymethyl butyrate and AB on the established human neuroblastoma cell lines SK-N-SH (panel A), NBAS-5 (panel B) and IMR-32(panel C) as a function of concentration (in $\mu$M).

The compounds herein described may have asymmetric centers. All chiral, diastereomeric, and racemic forms are included in the present invention. Many geometric isomers of olefins and the like can also be present in the compounds described herein, and all such stable isomers are contemplated in the present invention.

By "stable compound" or "stable structure" is meant herein a compound that is sufficiently robust to survive isolation to a useful degree of purity from a reaction mixture, and formulation into an efficacious therapeutic agent.

As used herein, "alkyl" means both branched- and straight-chain, saturated aliphatic hydrocarbon groups having the specified number of carbon atoms. As used herein "lower alkyl" means an alkyl group having 1 to 6 carbon atoms. As used herein, "alkenyl" means hydrocarbon chains of either a straight or branched configuration and one or more unsaturated carbon-carbon bonds, such as ethenyl, propenyl, and the like. Lower alkenyl is an alkenyl group having 2 to 6 carbon atoms. As used herein, "alkynyl" means hydrocarbon chains of either a straight or branched configuration and one or more carbon-carbon triple bonds, such as ethynyl, propynyl and the like.

Alkoxy, acyloxy and acylamino, respectively, as used herein, mean straight or branched chain lower alkoxy, lower alkylcarbonyloxy and lower alkylcarbonylamino groups.

As used herein, "aryl" includes "aryl" and "substituted aryl." Thus "aryl" of this invention means any stable 6- to 14-membered monocyclic, bicyclic or tricyclic ring, containing at least one aromatic carbon ring, for example, phenyl, naphthyl, indanyl, tetrahydronaphthyl (tetralin) and the like, optionally, substituted with, for example halo, alkyl, trifluoromethyl, alkoxy, hydroxy, carboxy, cyano, nitro, amino or acylamino groups.

As used herein, the term "heteroaryl" includes "heteroaryl" and "substituted heteroaryl." Thus "heteroaryl" of this invention means a stable 5-to 7-membered monocyclic or bicyclic heterocyclic ring which is aromatic, and which consists of carbon atoms and from 1 to 3 heteroatoms selected from the group consisting of N, O and S and wherein the nitrogen may optionally be quatemized, and including any bicyclic group in which any of the above-defined heteroaryl rings is fused to a benzene ring. The heteroaryl ring may be attached to its pendant group at any heteroatom or carbon atom which results in a stable structure. The heteroaryl rings described herein may be optionally substituted on carbon, on a nitrogen atom or other heteroatom if the resulting compound is stable and all the valencies of the atoms have been satisfied. The substituents of the substituted heteroaryl groups are as for the substituted aryl groups (see above). Examples of heteroaryl groups include, but are not limited to, pyridyl, pyrimidinyl, furanyl, thienyl, pyrrolyl, pyrazolyl, imidazolyl, tetrazolyl, benzofuranyl, benzothienyl, indolyl, indolenyl, quinolinyl, isoquinolinyl and benzimidazolyl.

As used herein "aralkyl" and "heteroaralkyl" refer to an aryl or heteroaryl group, respectively, as described above attached to an alkyl group as described above. Examples of heteroaralkyl groups include but are not limited to 2-, 3-, or 4-pyridylmethyl and 3-(2-, 3- or 4- pyridyl)propyl and the like.

The term "substituted", as used herein, means that one or more hydrogens on the designated atom are replaced with a selection from the indicated substituents, provided that the designated atom's normal valency is not exceeded, and that the substitution results in a stable compound.

The substituents of the invention include, as indicated, halo, hydroxy, alkyl, alkoxy, amino, acylamino, carboxy, carboxamide, carbalkoxy, carbonyl, cyano, nitro, and trifluoromethyl groups. These groups can be substituents for alkyl, alkenyl, alkynyl, aryl, aralkyl, heteroaryl, heteroaralkyl, and saturated heterocyclic groups as indicated in accordance with the invention. A halo group is a halogen, and includes fluoro, chloro, bromo and iodo groups. The alkyl moiety of alkoxy, acyl, aralkyl, heteroaralkyl and the like is lower alkyl unless otherwise specified.

As used herein, "therapeutically-effective amount" refers to that amount necessary to administer to a host to achieve an anti-tumor effect; to induce differentiation and/or inhibition of proliferation of malignant cancer cells, benign tumor cells or other proliferative cells; to aid in the chemoprevention of cancer; to promote wound healing; to treat a gastrointestinal disorder; to treat a blood disorder or increase the hemoglobin content of blood; to modulate an immune response; to enhance gene expression; to augment expression of tumor suppressor genes; to enhance insulin expression; to enhance chloride channel expression; to induce tolerance to an antigen; to prevent, treat or ameliorate protozoan infection; or to reduce pain and/or inflammation. Methods of determining therapeuticallyeffective amounts are well known.

As used herein, "pharmaceutically acceptable salts" refer to derivatives of the disclosed compounds that are modified by making acid or base salts. Examples include, but are not limited to, mineral or organic acid salts of basic residues such as amines; alkali or organic salts of acidic residues such as carboxylic acids, and the like.

Pharmaceutically-acceptable salts of the compounds of the invention can be prepared, for example by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salts of the invention can also be prepared by ion exchange, for example. Lists of suitable salts are found in *Remington's Pharmaceutical Sciences*, 17th ed., Mack Publishing Company, Easton, Pa., 1985, p. 1418, the disclosure of which is hereby incorporated by reference in its entirety.

The "pharmaceutical agents" for use in the methods of the invention related to the coadministration of compounds of Formula (I), include but are not limited to anticancer agents as well as differentiating agents. For example, the pharmaceutical agent can be a cytokine, an interleukin, an anti-cancer agent or anti-neoplastic agent, a chemotherapeutic agent, an antibody, a conjugated antibody, an immune stimulant, an antibiotic, a hormone antagonist or a growth stimulant. The pharmaceutical agent can also be a cytotoxic agent. Cytotoxic agents include antiviral nucleoside antibiotics such as ganciclovir, acyclovir, and famciclovir.

As used herein, the "chemotherapeutic agents" include but are not limited to alkylating agents, purine and pyrimidine analogs, vinca and vinca-like alkaloids, etoposide and etoposide-like drugs, corticosteroids, nitrosoureas, antimetabolites, platinum-based cytotoxic drugs, hormonal antagonists, anti-androgens and antiestrogens.

The "cytokines" for use herein include but are not limited to interferon, preferably α, β or γ interferon, as well as IL-2, IL-3, G-CSF, GM-CSF and EPO.

As used herein, an "immune stimulant" is a substance such as C. parvum or sarcolectin which stimulates a humoral or cellular component of the immune system.

The chemotherapeutic agents of the invention include but are not limited to tamoxifen, doxorubicin, I-asparaginase, dacarbazine, amsacrine, procarbazine, hexamethylmelamine, mitoxantrone and gemcitabine.

SYNTHETIC METHODS

The compounds of the present invention can generally be prepared by any method known in the art. For example, the compounds of the invention can be made by reacting the acid RCOOH with a reagent of the formula

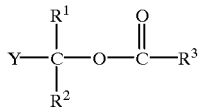

or by reacting the acid R³COOH with a reagent of the formula

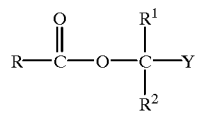

or by similar reactions between any of the appropriate acids and the appropriate alkyl halides, in the presence of a base, where Y is a leaving group such as halogen, methanesulfonate or p-toluenesulfonate and R, R¹, R² and R³ are as defined herein. The above reagents are readily prepared according to literature procedures, see for example, Nudelman et al., *J. Med. Chem.* 35:687–694, 1992, and Japanese patent 07033709 (1995). The base can be a trialkylamine, pyridine, an alkali metal carbonate or other suitable base. The reaction can be carried out in the presence or absence of an inert solvent. Suitable solvents include, for example, acetone, benzene, toluene, tetrahydrofuran, ethyl acetate, acetonitrile, dimethylformamide, dimethyl sulfoxide, chloroform, dioxane or 1,2-dichloroethane.

The procedures outlined above can be improved by one skilled in the art by, for instance, changing the temperature, duration, stoichiometry or other parameters of the reactions. Any such changes are intended to fall within the scope of this invention.

ACTIVITY

The activities of the compounds of the invention can be measured using generally-accepted techniques known to those skilled in the art consistent with the activity of interest. For example, the activity of compounds useful as differentiating agents can be measured using standard methodology of the nitro-blue tetrazolium reduction assay (e.g., Rabizadeh et al., *FEBS Lett.* 328:225–229, 1993; Chomienne et al., *Leuk. Res.* 10:631,1986; and Breitman et al. in *Methods for Serum-free Culture of Neuronal and Lymphoici Cells,* Alan R. Liss, NY, p. 215–236, 1984 which are hereby incorporated by reference in their entirety) and as described below. This in vitro assay has been deemed to be predictive and in fact correlative with in vivo efficacy (Castaigne et al., *Blood* 76:1704–1709, 1990).

Another assay which is predictive of differentiating activity is the morphological examination for the presence of Auer rods and/or specific differentiation cell surface antigens in cells collected from treatment groups, as described in Chomienne et al., (*Blood* 76:1710–1717, 1990 which is hereby incorporated by reference in its entirety) and as described below.

The compounds of the present invention also have antiproliferative and anti-tumor activity. The anti-proliferation activity of compounds of the present invention can be determined by methods generally known to those skilled in the art. Generally-accepted assays for measuring viability and anti-proliferative activity are the trypan blue exclusion test and incorporation of tritiated thymidine, also as described by Chomienne, et al., above, which is incorporated herein by reference. Other assays which predict and correlates antitumor activity and in vivo efficacy are the human tumor colony forming assay described in Shoemaker et al., *Can. Res.* 45:2145–2153, 1985, and inhibition of telomerase activity as described by Hiyayama et al., *J. Natl. Cancer Inst.* 87:895–908,1995, which are both incorporated herein by reference in their entirety. These assays are described in further detail below.

The compounds of the invention are generally oxyalkylene ester compounds having covalently attached thereto an acyl moiety that inhibits beta-oxidation of fatty acids. The acyl component may be, for example, that of a cyclooxygenase 1 or 2 inhibitor which acts on the arachidonic acid cascade, such as a salicylic acid derivative such as salsalate, diflunisal, sulfasalazine, an indole or indene acetic acid, such as indomethacin, sulindac, etodolac, and the like; a heteroaryl acetic acid such as tolmetin, diclofenac, or ketorolac; an anthranilic acid such as mefenamic acid or meclofenamic acid; or a propionic acid derivative such as naproxen, flurbiprofen, ketoprofen, fenoprofen, oxaprozin and the like. A preferred compound of the invention is α-methyl-4-(2-methylpropyl)-benzeneacetyloxymethyl butyrate. Other preferred compounds of the invention include 1-{α-methyl-4-(2-methylpropyl)-benzeneacetyloxy}-ethyl butyrate,1{α-methyl-4-(2-methylpropyl)-benzeneacetyloxy}-butyl butyrate, 6-methoxy-α-methyl-2-naphthaleneacetyloxylmethyl butyrate, 1-{6-methoxy-α-methyl-2-naphthaleneacetyloxylmethy}-ethyl butyrate and 1-{6-methoxy-α-methyl-2-naphthaleneacetyloxy}-butyl butyrate.

The acyl-containing oxyalkylene ester compounds of the present invention have enhanced activity, i.e., enhanced stability, and exhibit longer duration of action than known oxyalkylene ester compounds, butyric acid, sodium butyrate and arginine butyrate. For example, butyric acid exhibits a very short duration of activity, approximately one minute, whereas the present compounds are significantly longer active. The oxyalkylene ester moiety of the compounds of the invention is an inhibitor of beta-oxidation of the fatty acid chain. It is believed that the covalent attachment of a beta-oxidation inhibitor in the present compounds is responsible, at least in part, for the enhanced stability and potency of these compounds.

Cell Cultures

Human promyelocytic leukemia cells (HL-60), human pancreatic carcinoma cells (PaCa-2) and human breast adenocarcinoma cells, pleural effusion cells (MCF-7) can be cultured as follows. Cells are grown in RPMI media with 10% FCS, supplemented with 2 mM glutamine and incubated at 37° C. in a humidified 5% $CO_2$ incubator. Alternatively, cells can be grown in any other appropriate growth medium and conditions which support the growth of the cell line under investigation. Viability can be determined by trypan blue exclusion. Cells are exposed to a test compound, cultures are harvested at various time points following treatment and stained with trypan blue.

Cellular Staining to Detect Differentiation

Lipid staining and/or immunochemical staining of casein can be used as a marker for cellular differentiation of breast cancer cells (Bacus et al., *Md. Carcin.* 3:350–362, 1990). Casein detection can be done by histochemical staining of breast cancer cells using a human antibody to human casein as described by Cheung et al., *J. Clin. Invest.* 75:1722–1728, which is incorporated by reference in its entirety.

Nitro-Blue Tetrazolium (NBT) Assay

Cell differentiation of myeloid leukemia cells can be evaluated, for example, by NBT reduction activity as follows. Cell cultures are grown in the presence of a test compound for the desired time period. The culture medium is then brought to 0.1% NBT and the cells are stimulated with 400 mM of 12-O-tetradecanoyl-phorbol-13-acetate (TPA). After incubation for 30 min at 37° C., the cells are examined microscopically by scoring at least 200 cells. The capacity for cells to reduce NBT is assessed as the percentage of cells containing intracellular reduced black formazan deposits and corrected for viability.

Cell Surface Antigen Immunophenotyping

Cell surface antigen immunotyping can be conducted using dual-color fluorescence of cells gated according to size. The expression of a panel of antigens from early myeloid (CD33) to late myeloid can be determined as described in Warrell, Jr. et al., *New Engl. J. Med.* 324:1385–1392, 1992, which is incorporated by reference herein in its entirety.

Apoptosis Evaluation

Apoptosis can be evaluated by DNA fragmentation, visible changes in nuclear structure or immunocytochemical analysis of Bcl-2 expression.

DNA fragmentation can be monitored by the appearance of a DNA ladder on an agarose gel. For example, cellular DNA is isolated and analyzed by the method of Martin et al., *J. Immunol.*, 145:1859–1867, 1990 which is incorporated by reference herein in its entirety.

Changes in nuclear structure can be assessed, for example, by acridine orange staining method of Hare et al., *J. Hist. Cyt.*, 34:215–220, 1986 which is incorporated by reference herein in its entirety.

Immunological detection of Bcl-2 can be performed on untreated cells and cells treated with the test compound. HL60 cells are preferred but other cell lines capable of expressing Bcl-2 can be used. Cytospins are prepared and the cells are fixed with ethanol. Fixed cells are reacted overnight at 4° C. with the primary monoclonal antibody, anti-Bcl-2 at a dilution of 1:50. Stainirig is completed to visualize antibody binding, for example, using Strep A-B Universal Kit (Sigma) in accordance with the manufacturer's instructions. Identically-treated cells which received no primary antibody can serve as a non-specific binding control. Commercial kits are also available and can be used for detecting apoptosis, for example, Oncor's Apop Tag®.

Modulation of Gene Expression

The levels of expression from oncogene and tumor suppressor genes can be evaluated by routine methods known in the art, such as Northern blotting of RNA, immunoblotting of protein and PCR amplification.

Mouse Cancer Model

Compounds can be examined for their ability to increase the life span of animals bearing B16 melanomas, Lewis lung carcinomas and myelomonocytic leukemias as described in Nudelman et al., *J. Med. Chem.* 35:687–694, 1992, or Rephaeli et al., *Int. J. Cancer* 49:66–72, 1991, which are incorporated by reference herein in their entireties.

For example, the efficacy of compounds of the present invention in a leukemia model can be tested as follows: Balbic mice are injected with WEHI cells and a test compound or control solution is administered the following day. The life span of the treated animals is compared to that of untreated animals.

The efficacy of compounds of the present invention on primary tumors can also be tested with subcutaneously implanted lung carcinoma or B16 melanoma by measuring the mass of the tumor at the site of implantation every two weeks in control and treated animals.

The efficacy of compounds in xenografts can be determined by implanting the human tumor cells subcutaneously into athymic mice. Human tumor cell lines which can be used include, but are not limited to, prostate carcinoma (human Pc-3 cells), pancreatic carcinoma (human Mia PaCa cells), colon adenocarcinoma (human HCT-15 cells) and mammary adenocarcinonia (human MX-I cells). Treatment with control solution or a test compound of the invention begins, for example, when tumors are approximately 100 mg. Anti-tumor activity is assessed by measuring the delay in tumor growth, and/or tumor shrinking and/or increased survival of the treated animals relative to control animals.

Telomerase Activity

A high level of telomerase activity is associated with the high proliferation rate found in cancer cells. Compounds which inhibit telomerase activity result in inhibition of cancer cell growth and de-differentiation. Commercially available telomerase assays can thus be used to assess the anticancer activities of compounds on cancer cell lines.

Chemoprevention

The chemoprevention activity of the compounds of the invention can be determined in the two-stage mouse carcinogenesis model of Nishimo et al. (supra).

Assay of Compounds

Compounds of the invention, their salts or metabolites, can be measured in a biological sample by any method known to those skilled in the art of pharmacology, clinical chemistry or the like. Such methods for measuring these compounds are standard methods and include, but are not limited to high performance liquid chromatography (HPLC), gas chromatography (GC), gas chromatography mass spectroscopy (GC-MS), radioimmunoassay (RIA), and others.

Stability of Compounds

The metabolism of the compounds of this invention is analyzed by administering radiolabelled compound by intravenous, intraperitoneal or per os route to a mouse and identifying the nature and quantity of radiolabelled compound released in the blood, excreta, tissues and during respiration.

C57BI/6 mice are injected with 20–500 mg/kg of a test compound (5 $\mu$Ci) arnd placed in metabolic cages so thatexpired $CO_2$ and volatile organics can be trapped chemically. Blood, urine and feces are collected at various times. Total radioactivity in the blood, urine, expired $CO_2$, and volatile traps is determined by solubilizing the sample and scintillation counting. Feces and carcasses are homogenized and subjected to scintillation to determine total radioactivity.

Blood samples are extracted with acetonitrile and run on a high performance liquid chromatography)HPLC) system to separate radiolabelled test compound, butyric acid and other metabolites. The amount of radioactivity is determined with an on-line scintillation flow detector. HPLC fractions are also collected and subjected to scintillation counting. The clearance of the test compound from the blood is monitored and its half-life estimated.

Dosage and Formulation

The compounds of the present invention can be administered to a mammalian patient to treat cancer or in any other method of the invention which involves treating a patient by any means that produces contact of the active agent with the agent's site of action in the body of the subject. Mammalian patients include humans and domestic animals. The compounds of the invention can be administered by any conventional means available for use in conjunction with pharmaceuticals, either as individual therapeutic agents or in a combination of therapeutic agents. The compounds can be administered alone, but are generally administered with a pharmaceutical carrier selected on the basis of the chosen route of administration and standard pharmaceutical practice. The pharmaceutical compositions of the invention may be adapted for oral, parenteral, transdermal, transmucosal, rectal or intranasal administration, and may be in unit dosage form, as is well known to those skilled in the pharmaceutical art. The term "parenteral" as used herein includes subcutaneous, intravenous, intramuscular, or intrasternal injection or infusion techniques.

The appropriate dosage administered in any given case will, of course, vary depending upon known factors, such as the pharmacodynamic characteristics of the particular agent and its mode and route of administration; the age, general health, metabolism, weight of the recipient and other factors which influence response to the compound; the nature and extent of the symptoms; the kind of concurrent treatment; the frequency of treatment; and the effect desired. A daily dosage of active ingredient can be expected to be about 10 to 10,000 milligrams per meter$^2$ of body mass (mg/m$^2$, with the preferred dose being 50–5,000 mg/m$^2$ body mass.

Dosage forms (compositions suitable for administration) contain from about 1 mg to about 1 g of active ingredient per unit. In these pharmaceutical compositions the active ingredient will ordinarily be present in an amount of about 0.5–95% by weight based on the total weight of the composition.

The active ingredient can be administered orally in solid or semi-solid dosage forms, such as for example hard or soft-gelatin capsules, tablets, and powders, or in liquid dosage forms, such as elixirs, syrups, disperse powders or granules, emulsions, and aqueous or oily suspensions. It can also be administered parenterally, in sterile liquid dosage forms. Other dosage forms include transdermal administration via a patch mechanism or ointment.

Compositions intended for oral use may be prepared according to any methods known to the art for the manufacture of pharmaceutical compositions and such compositions may contain one or more agents including sweetening agents, flavoring agents, coloring agents, and preserving agents in order to provide a pharmaceutically elegant and palatable preparation.

Tablets contain the active ingredient in admixture with non-toxic pharmaceutically acceptable excipients which are suitable for the manufacture of tablets. Such excipients may include, for example, inert diluents, such as calcium phosphate, calcium carbonate, sodium carbonate, sodium phosphate, or lactose; granulating disintegrating agents, for example, maize starch or alginic acid; binding agents, such as starch, gelatin, or acacia; and lubricating agents, for example, magnesium stearate, stearic acids or talc. Compressed tablets may be uncoated or may be sugar coated or film coated by known techniques to mask any unpleasant taste and protect the tablet from the atmosphere, or enteric coated for selective disintegration and adsorption in the gastrointestinal tract.

Hard gelatin capsules or liquid filled soft gelatin capsules contain the active ingredient and inert powdered or liquid carriers, such as, but not limited to calcium carbonate, calcium phosphate, kaolin, lactose, lecithin starch, cellulose derivatives, magnesium stearate, stearic acid, arachis oil, liquid paraffin, olive oil, pharmaceutically-accepted synthetic oils and other diluent, suitable for the manufacture of capsules. Both tablets and capsules can be manufactured as sustained release-products to provide for continuous release of medication over a period of hours.

Aqueous suspensions contain the active compound in admixture with excipients suitable for the manufacture of aqueous suspensions. Such excipients are suspending agents, e.g., sodium carboxymethylcellulose, methylcellulose, hydroxypropylmethylcellulose, sodium alginate, polyvinylpyrrolidone, gum tragacanth, and gum acacia; dispersing or wetting agents, such as a naturally occurring phosphatide, e.g., lecithin, or condensation products of an alkylene oxide with fatty acids, for example polyoxyethylene stearate, or a condensation products of ethylene oxide with long chain aliphatic alcohols, e.g., heptadecaethyleneoxycetanol, or condensation products of ethylene oxide with partial esters derived from fatty acids and a hexitol, e.g., polyoxyethylene sorbitol monooleate, or a condensation product of ethylene oxide with partial esters derived from fatty acids and hexitol anhydrides, e.g., polyoxyethylene sorbitan monooleate. The aqueous suspensions can also contain one or more preservatives, for example ethyl, n-propyl, or p-hydroxy benzoate, one or more coloring agents, one or more flavoring agents, and one or more sweetening agents, such as sucrose, saccharin, or sodium or calcium cyclamate.

Dispersable powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring, and coloring agents, can also be present.

Syrups and elixirs can be formulated with sweetening agents, such as, glycerol, sorbitol or sucrose. Such formulations may also contain a demulcent, a preservative and flavoring and coloring agents.

The pharmaceutical compositions can be in the form of a sterile injectable preparation, for example as a sterile injectable aqueous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent, for example, as a solution in 1,3-butanediol.

In general, water, a suitable oil, saline, aqueous dextrose (glucose), polysorbate and related sugar solutions, emulsions, such as Intralipid® (Cutter Laboratories, Inc., Berkeley, Calif.) and glycols such as propylene glycol or polyethylene glycols are suitable carriers for parenteral solutions. Antioxidizing agents, such as but not limited to sodium bisulfite, sodium sulfite, or ascorbic acid, either alone or combined, are suitable stabilizing agents. Also used can be citric acid and its salts and sodium EDTA. In addition, parenteral solutions can contain preservatives, such as but not limited to benzalkonium chloride, methyl- or propyl-paraben, and chlorobutanol.

The pharmaceutical compositions of the present invention also include compositions for delivery across cutaneous or mucosal epithelia including transdermal, intranasal, sublingual, buccal, and rectal administration. Such compositions may be part of a transdermal device, patch, topical formulation, gel, etc., with appropriate excipients. Thus, the compounds of the present invention can be compounded with a penetration-enhancing agent such as 1-n-dodecylazacyclopentan-2-one or the other penetration-enhancing agents disclosed in U.S. Pat. Nos. 3,991,203 and 4,122,170 which are hereby incorporated by reference in their entirety to describe penetration-enhancing agents which can be included in the transdermal or intranasal compositions of this invention.

Suitable pharmaceutical carriers are described in *Remington's Pharmaceutical Sciences,* Mack Publishing Company, a standard reference text in this field, which is incorporated herein by reference in its entirety.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited patents or publications may provide further useful information these cited materials are hereby incorporated by reference in their entirety.

EXAMPLE 1

Synthesis of α-methyl4-(2-methylpropyl)-benzeneacetyloxymethyl butyrate. (Compound 1)

To a stirred solution of ibuprofen (10.16 g, 49 mmol) and chloromethyl butyrate (6.80 g, 1 eq.) in dry dimethylformamide (20 mL), under nitrogen, was dropwise added triethylamine (8.5 mL, 6 g, 1.2 eq). The mixture was heated at 70° C. for four hours, during which time a large amount of precipitate formed; thin layer chromatography (TLC: ethyl acetate:hexane 1:1) showed that all of the acid had reacted. The precipitate was filtered and washed with ethyl acetate. The filtrate was partitioned between water and ethyl acetate. The aqueous phase was washed with a small amount of ethyl acetate and the combined organic phase was washed with water (3 x), 5% solution of sodium bicarbonate (2 x), and brine (2 x), dried with magnesium sulfate and evaporated to give the crude product as a colorless oil (11.6 g). The crude product was distilled at 170° C./1 mm Hg. The pure product was obtained as a colorless oil (8.7 g, 58% yield).

EXAMPLE 2

Synthesis of Various NSAID-Containinq Compounds of the Invention

The compounds in Table 1 below are synthesized by the procedures described in Example 1 above.

TABLE 1

$$R-\overset{O}{\underset{}{C}}-O-\overset{R^1}{\underset{R^2}{C}}-O-\overset{O}{\underset{}{C}}-R^3$$

| R | $R_1$ | $R_2$ | $R_3$ | $R^3$ COOH Generic Name |
|---|---|---|---|---|
| n-$C_3$—$H_7$— | $CH_3$ | H | —CH(CH$_3$)—C$_6$H$_4$—CH$_2$CH(CH$_3$)$_2$ | Ibuprofen |
| 4-$C_6H_5$—$C_3H_6$— | n-$C_4$—$H_9$ | H | —CH(CH$_3$)—C$_6$H$_4$—CH$_2$CH(CH$_3$)$_2$ | Ibuprofen |

TABLE 1-continued $$R-\overset{O}{\underset{}{C}}-O-\overset{R^1}{\underset{R^2}{C}}-O-\overset{O}{\underset{}{C}}-R^3$$

| R | R₁ | R₂ | R₃ | R³ COOH Generic Name |
|---|---|---|---|---|
| $C_6H_5(CH_2)_3-$ | $CH_3$ | H | (2-methyl-4-hydroxyphenyl)-(2,4-difluorophenyl) structure | Diflunisal |
| $CH_2=CHCH_2-$ | $CH_3$ | $CH_3$ | indomethacin structure (indole with OCH₃, CH₃, CH₂, N-C(=O)-C₆H₄-Cl) | Indomethacin |
| $Cl(CH_2)_2-$ | H | H | naproxen structure (6-methoxynaphthalene with CH(CH₃)) | Naproxen |
| 2-pyridyl-CH₂— | $C_2H_5$ | H | 2-(OAc)phenyl structure | Aspirin |
| $C_6H_5CH_2CH_2CH_2-$ | $n$-$C_3H_7$ | H | ibuprofen structure (–CH(CH₃)–C₆H₄–CH₂CH(CH₃)₂) | Ibuprofen |
| $n$-$C_3$—$H_7$— | H | H | naproxen structure | Naproxen |
| $n$-$C_3H_7$— | $CH_3$ | H | naproxen structure | Naproxen |

EXAMPLE 3

Inhibition of Clonogenicity of Established Tumor Cell Lines

The cell lines that were studied are listed in Table 2.

TABLE 2

| Cell Lines | Origin |
|---|---|
| MCF-7 | Breast Carcinoma |
| CFPAC | Pancreatic Carcinoma |
| OVCAR-5 | Ovarian Carcinoma |
| LOX IMVI | Melanoma |
| K562 | Erytholeukemia |
| SK-N-SH | Neuroblastoma |
| NBAS-5 | Neuroblastoma |
| PMR-32 | Neuroblastoma |

TABLE 2-continued

| Cell Lines | Origin |
|---|---|
| LA1-5S | Neuroblastoma |
| NBL-W-N | Neuroblastoma |
| SMS-KAN | Neuroblastoma |
| SK-N-MC | Neuroblastoma |

Inhibition of cancer cell growth in agar culture—clonogenicity was tested using cell lines as follows:

The neuroblastoma cell lines were grown to 70–80% confluence in RPMI 1640, 10% fetal calf serum, 100 IU penicillin, 100 μg streptomycin and 2 mM L-glutamine (complete media). Cells were harvested, washed in complete media, and counted. Cell viability was determined by trypan blue exclusion.

The cells were placed into soft agar (0.12% in media) and plated at 5,000 viable cells per well onto an agarose underlayer (0.4%) in 24-well plates. After overnight culture, AB or α-methyl-4-(2-methylpropyl)-benzeneacetyloxymethyl butyrate was added at the indicated concentration. The control cells received media alone. As a control for complete cell death, plated cells were treated with a superlethal dose of 10 μg/ml of cisplatin. The dose which inhibited fifty percent or ninety percent of cell growth ($IC_{50}$ or $IC_{90}$) was calculated using the Chou Analysis Median Effective Dose equation.

Figure 1B:
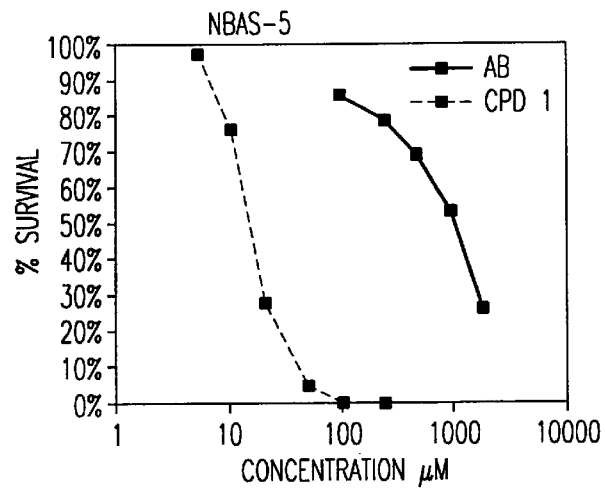
Figure 1C:
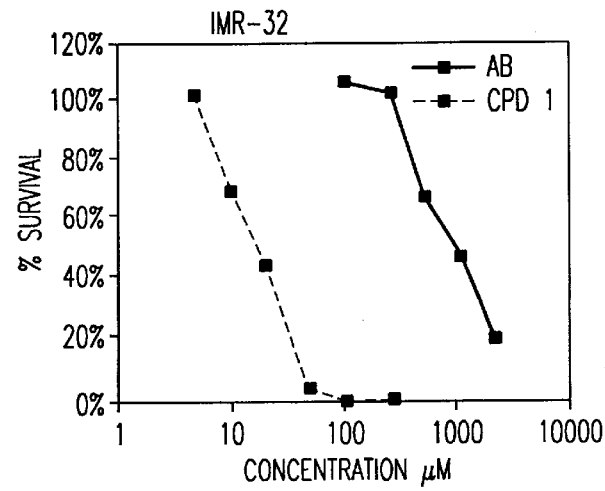
Figure 2A:
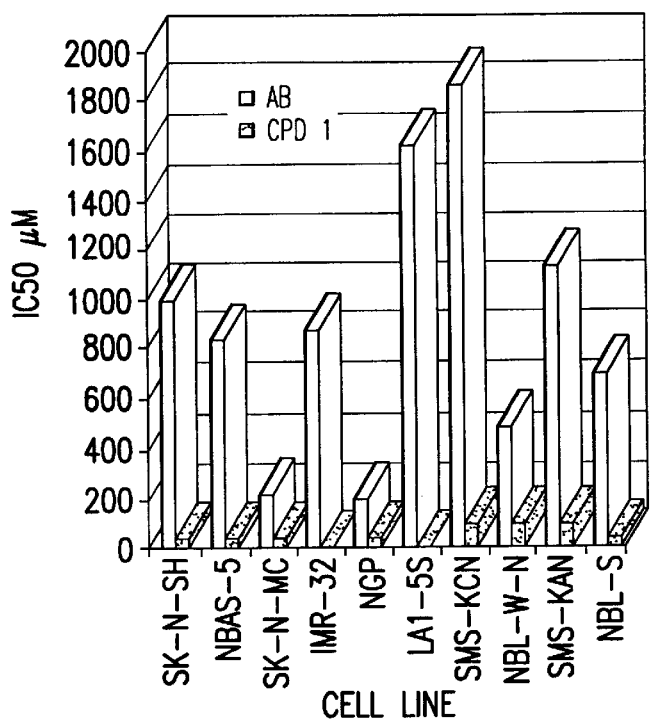
FIGS. 2A and 2B, respectively, are graphic illustrations showing the $IC_{50}$ and $IC_{90}$ of α-methyl-4-(2-methylpropyl)-benzeneacetyloxymethyl butyrate and AB on established human neuroblastoma cell lines.
Figure 2B:
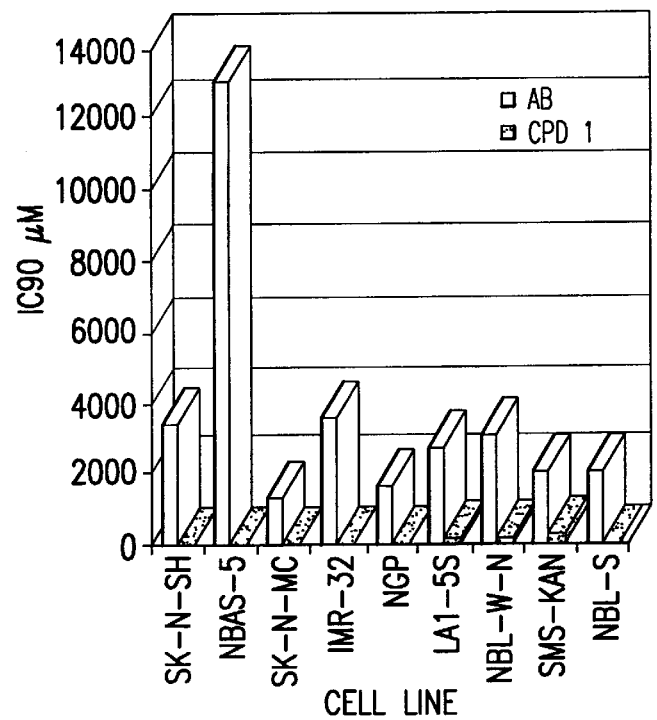
Figure 3A:
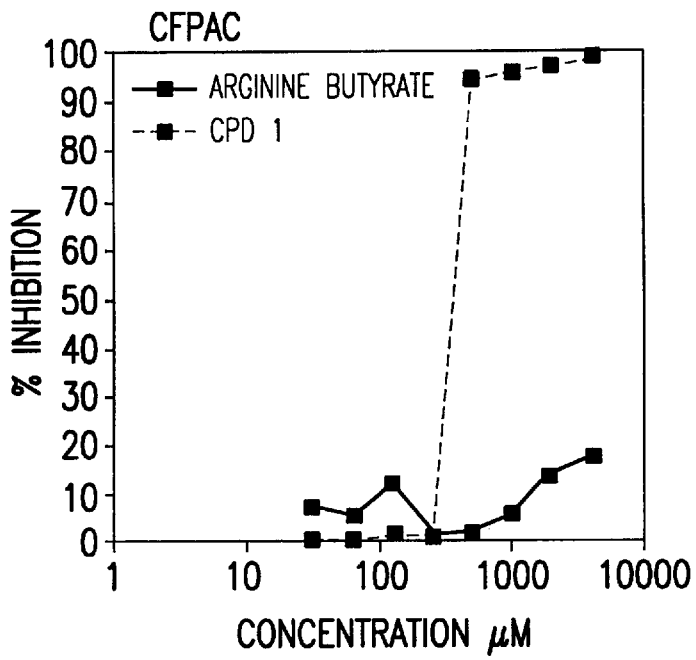
FIGS. 3A–3D are graphic illustrations showing cancer cell growth inhibition measured by the sulforhodamine method (SRB) as described by Monks, et al., JNCI; 83: 757–766.
Figure 3B:
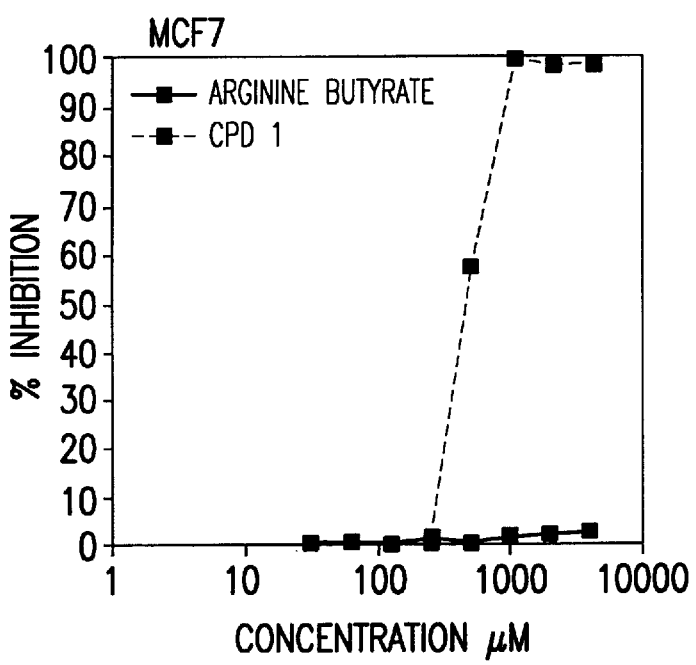
Figure 3C:
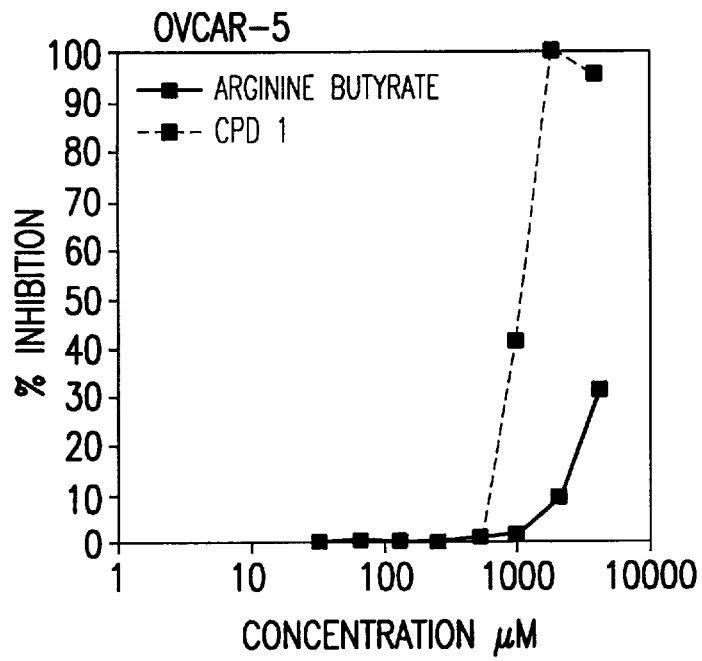
Figure 3D:
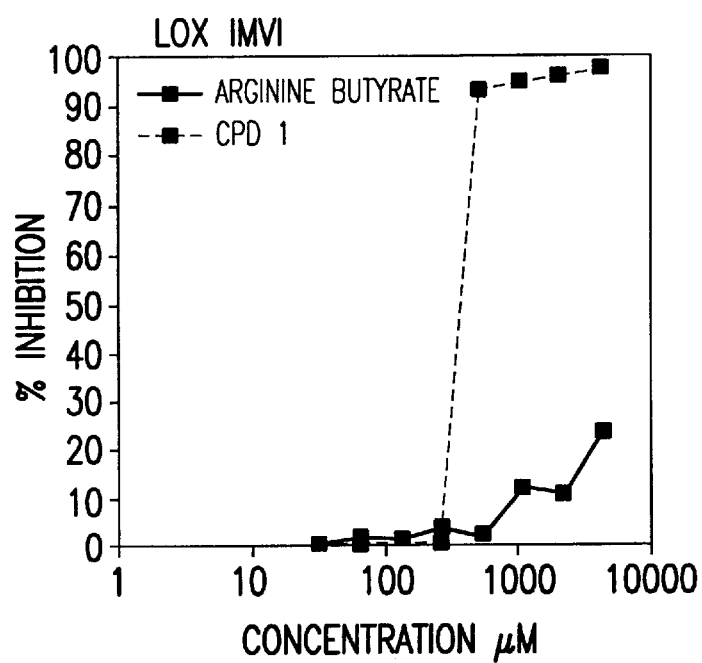

The clonogenicity results are expressed as the percentage of clones relative to media-treated control cultures for α-methyl-4-(2-methylpropyl)-benzeneacetyloxymethyl butyrate and AB, respectively (Table 3) and graphically for the neuroblastoma cell lines in FIG. 1. Comparison between AB and α-methyl-4-(2-methylpropyl)-benzeneacetyloxymethyl butyrate shows that the cells are inhibited by both AB and α-methyl-4(2-methylpropyl)-benzeneacetyloxymethyl butyrate in dose-dependent manner, however, they are mostly an order of magnitude more sensitive to α-methyl4-(2-methylpropyl)-benzeneacetyloxymethyl butyrate. The $IC_{50}$ and $IC_{90}$ values for each cell line are provided in Table 4 and graphically in FIG. 2. The ratio between the $IC_{50}$ of AB/α-methyl-4-(2-methylpropyl)-benzeneacetyloxymethyl butyrate ranges between 7–63 fold and has a maiden value of 16. The ratio between the $IC_{90}$ of AB/α-methyl-4-(2-methylpropyl)-benzeneacetyloxymethyl butyrate ranges between 7–434 and has a maiden value of 32. These results demonstrate that α-methyl-4-(2-methylpropyl)-benzeneacetyloxymethyl butyrate is a significantly more potent tumor cell clonogenicity inhibitor than AB. The difference between AB and α-methyl-4-(2-methylpropyl)-benzeneacetyloxymethyl butyrate is even more pronounced when the $IC_{90}$ is compared. The significance of $IC_{90}$ rests in its clinical implication for eradication of cancer residual disease.

TABLE 3

THE EFFECT OF ARGININE BUTYRATE (AB) AND
α-METHYL-4-(2-METHYLPROPYL)-BENZENEACETYLOXYMETHYL BUTYRATE (COMPOUND 1)
ON THE CLONOGENICITY OF THREE NEUROBLASTOMA CELL LINES

| CELL LINE | DRUG μM | 10 | 20 | 50 | 100 | 250 | 500 | 1000 | 2000 |
|---|---|---|---|---|---|---|---|---|---|
| SK-N-SH | AB | | | | 0.99 ± 0.01 | 0.81 ± 0.01 | 0.75 ± 0.09 | 0.54 ± 0.02 | 0.24 ± 0.01 |
| | Compound 1 | 0.66 ± 0.04 | 0.50 ± 0.0 | 0.05 ± 0.0 | 0.01 ± 0.01 | 0.0 ± 0.0 | | | |
| NBAS-5 | AB | | | | 0.85 ± 0.01 | 0.78 ± 0.02 | 0.68 ± 0.02 | 0.53 ± 0.02 | 0.25 ± 0.01 |
| | Compound 1 | 0.76 ± 0.07 | 0.27 ± 0.15 | 0.03 ± 0.0 | 0 ± 0 | 0 ± 0 | | | |
| IMR-32 | AB | | | | 1.08 ± 0.0 | 1.04 ± 0.0 | 0.69 ± 0.07 | 0.49 ± 0.03 | 0.21 ± 0.01 |
| | Compound 1 | 0.71 ± 0.10 | 0.46 ± 0.08 | 0.03 ± 0.01 | 0 ± 0 | 0 ± 0 | | | |

TABLE 4

The $IC_{50}$ AND $IC_{90}$ VALUES OF ARGININE BUTYRATE (AB) AND
αMETHYL-4-(2-METHYLPROPYL)-BENZENEACETYLOXYMETHYL BUTYRATE (COMPOUND 1)
IN HUMAN NEUROBLASTOMA CELL LINES

| μM | DRUG CELL LINE | SK-N-SH | NBAS-5 | SK-N-MC | IMR-32 | NGP | LA1-5S | SMS-KCN | NBL-W-N | SMS-KAN | NBL-S |
|---|---|---|---|---|---|---|---|---|---|---|---|
| $IC_{50}$ | AB | 998 | 833 | 215 | 881 | 197 | 1627 | 1872 | 489 | 1138 | 701 |
| | Compound 1 | 16 | 15 | 24 | 15 | 15 | 29 | 118 | 46 | 77 | 24 |
| | AB/Compound 1 | 63.37 | 55.53 | 9 | 59 | 67.9 | 56 | 15.86 | 10.6 | 14.7 | 29.2 |
| $IC_{90}$ | AB | 3397 | 13030 | 1314 | 3566 | 1622 | 2675 | | 3074 | 2079 | 2003 |
| | Compound 1 | 39 | 30 | 148 | 32 | 87 | 84 | | 134 | 289 | 61 |
| | AB/ | 87 | 434 | 887 | 111437 | 18.46 | 31.8 | | 22.9 | 7.2 | 32.8 |

EXAMPLE 4
Inhibition of Cancer Cell Growth

Inhibition of cancer cell growth was measured by the sulforhodamine B (SRB) method as described by Monks et al., J. Nat. Canc. Inst., (1991), 83: 757–766, incorporated herein in its entirety. The SRB assay is recognized by the National Institute for Cancer (NCI) as a reliable screen for anticancer drugs and is used by the NCI for this purpose. The effect of α-methyl-4-(2-methylpropyl)-benzeneacetyloxymethyl butyrate was compared to that of AB (Table 5). α-Methyl-4-(2-methylpropyl)-benzeneacetyloxymethyl butyrate exhibited at least 100 fold greater activity than that of AB. (FIGS. 3A–3D).

TABLE 5

THE EFFECT OF ARGININE BUTYRATE AND α-METHYL-4-(2-METHYLPROPYL)-BENZENEACETYLOXYMETHYL BUTYRATE ON THE GROWTH OF HUMAN PANCREATIC, OVARIAN, BREAST CARCINOMA AND MELANOMA CELL LINES

| | CFPAC % INHIBITION | | | | MCF7 % INHIBITION | | | |
|---|---|---|---|---|---|---|---|---|
| | AB | | COMPOUND 1 | | AB | | COMPOUND 1 | |
| Dosage (nM) | MEAN | SD | MEAN | SD | MEAN | SD | MEAN | SD |
| 0.00000 | 0.0 | 2.6 | 0.0 | 0.5 | 0.0 | 0.7 | 0.0 | 7.0 |
| 0.03125 | 6.6 | 7.3 | 0.0 | 1.5 | 0.3 | 0.4 | 0.0 | 4.9 |
| 0.06250 | 4.8 | 8.9 | 0.1 | 1.1 | 0.2 | 0.4 | 0.0 | 3.8 |
| 0.12500 | 11.3 | 6.8 | 1.1 | 0.6 | 0.0 | 0.6 | 0.0 | 4.4 |
| 0.25000 | 1.0 | 1.6 | 0.0 | 2.7 | 0.1 | 0.6 | 1.1 | 7.5 |
| 0.50000 | 1.5 | 5.5 | 93.3 | 4.2 | 0.0 | 0.6 | 57.8 | 7.5 |
| 1.00000 | 4.7 | 2.8 | 94.9 | 2.7 | 1.2 | 0.4 | 99.3 | 0.4 |
| 2.00000 | 12.8 | 7.0 | 96.0 | 2.7 | 1.8 | 0.0 | 98.9 | 0.3 |
| 4.00000 | 16.6 | 6.5 | 97.4 | 1.6 | 2.2 | 0.4 | 98.7 | 0.2 |

| | OVCAR-5 % INHIBITION | | | | LOX IMVI % INHIBITION | | | |
|---|---|---|---|---|---|---|---|---|
| | AB | | COMPOUND 1 | | AB | | COMPOUND 1 | |
| Dosage (nM) | MEAN | SD | MEAN | SD | MEAN | SD | MEAN | SD |
| 0.00000 | 0.0 | 0.5 | 0.0 | 0.5 | 0.0 | 0.5 | 0.0 | 0.5 |
| 0.03125 | 0.0 | 0.5 | 0.0 | 0.3 | 0.0 | 0.8 | 0.0 | 1.5 |
| 0.06250 | 0.1 | 0.5 | 0.3 | 0.7 | 1.4 | 1.0 | 0.1 | 1.1 |
| 0.12500 | 0.5 | 0.3 | 0.5 | 0.6 | 1.5 | 1.2 | 1.5 | 0.6 |
| 0.25000 | 0.3 | 0.4 | 0.0 | 2.5 | 3.1 | 2.3 | 0.0 | 2.7 |
| 0.50000 | 1.3 | 0.5 | 0.9 | 0.9 | 1.8 | 1.1 | 93.3 | 4.2 |
| 1.00000 | 2.5 | 0.5 | 39.7 | 24.1 | 11.8 | 7.4 | 94.9 | 2.7 |
| 2.00000 | 6.6 | 1.1 | 99.8 | 1.8 | 10.7 | 7.2 | 96.0 | 2.7 |
| 4.00000 | 29.3 | 3.0 | 95.1 | 3.6 | 23.3 | 6.0 | 97.4 | 1.6 |

EXAMPLE 5
In Vitro Stability of Compound 1 in Human Blood

Figure 4:
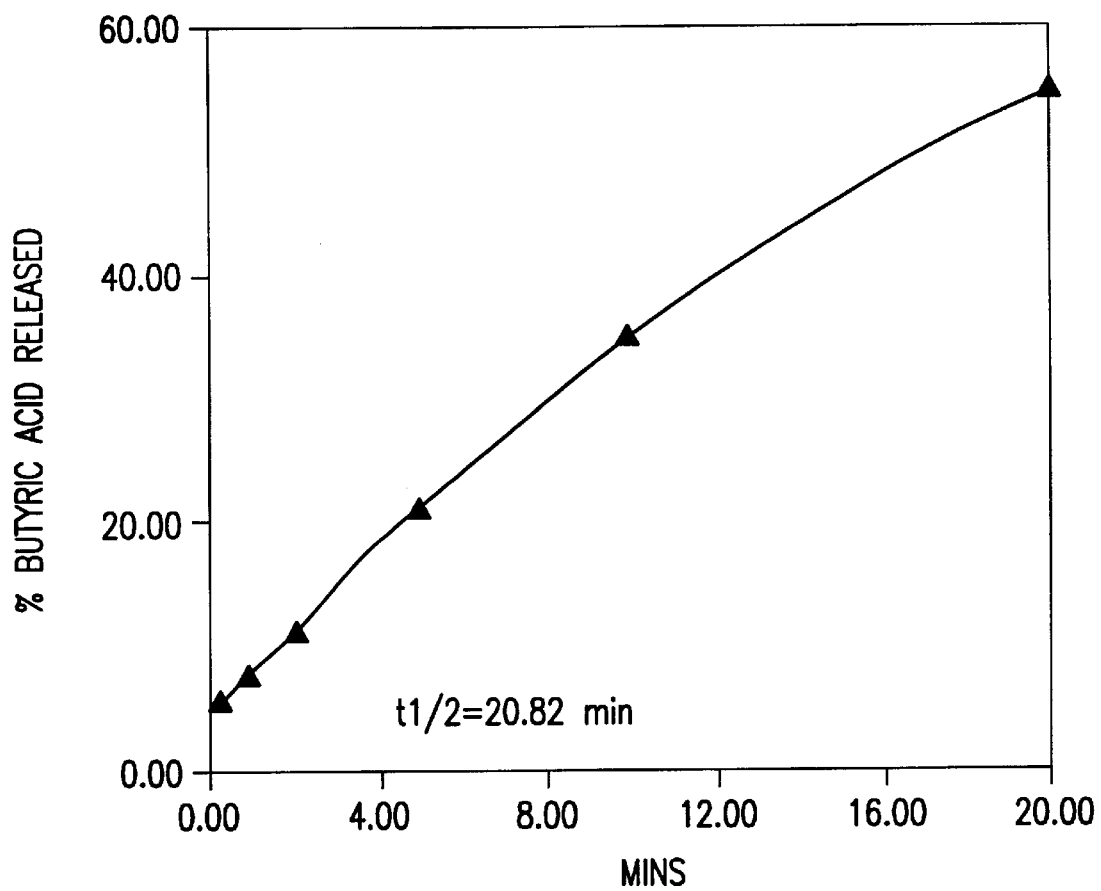
FIG. 4 is a graph of the amount of butyric acid released from α-methyl-4-(2-methylpropyl)-benzeneacetyloxymethyl butyrate over time in vitro.

Radiolabelled Compound 1 (5 μCi) was added to 1 mL of whole human blood and allowed to stand for various times. The samples were quenched with acetonitrile and prepared as previously described. The data are shown in FIG. 4.

The calculated half time of Compound 1 is about 20.82 minutes.

What is claimed is:

1. A compound represented by the formula:

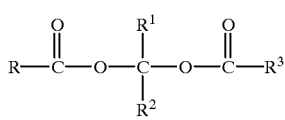

(I)

wherein

R is a $C_1$ to $C_{10}$ alkyl, $C_2$ to $C_{10}$ alkenyl or $C_2$ to $C_{10}$ alkynyl group, optionally substituted with an alkoxy, halo, trifluoromethyl, amino, acylamino, carboxyl, carboxamide, carbalkoxy, hydroxy, acyl, aryl, substituted aryl, heteroaryl or substituted heteroaryl group;

$R^1$ and $R^2$ are each independently H, $C_1$ to $C_6$ straight or branched chain alkyl, $C_2$ to $C_6$ branched or straight chain alkenyl or $C_2$ to $C_6$ branched or straight chain alkynyl wherein the alkyl, alkenyl or alkynyl group is optionally substituted with halo or alkoxy; and $R^3CO$ is an acyl moiety of a carboxylic acid-containing compound that inhibits beta-oxidation of fatty acids;

with the proviso that when said acyl moiety is the acyl moiety of a NSAID compound, the NSAID is selected from the group consisting of ketoprofen, diflunisal, salsalate, etodolac, tolmetin, ibuprofen, naproxen, oxaprozin, salicylic acid, acetylsalicylic acid, indomethacin, flurbiprofen, diclofenac, mefenamic acid, meclofenamic acid, ketorolac and sulindac; and wherein when the acyl moiety is that of ibuprofen, R is not methyl or ethyl; when the acyl moiety is that of oxaprozin, R is not methyl; when the acyl moiety is that of sulindac or naproxen, R is not alkyl; when the acyl moiety is that of salicylic acid or acetylsalicylic acid, R is $C_3$ to $C_{10}$ alkenyl or lower haloalkyl; and when the acyl moiety is that of indomethacin, flurbiprofen, mefenamic acid, meclofenamic acid or diclofenac, R is $C_3$ to $C_{10}$ haloalkyl, aralkyl, heteroaralkyl, 2-, 3- or 4-arylpropyl or 2-, 3- or 4heteroarylpropyl;

or a pharmaceutically acceptable salt thereof.

2. The compound of claim 1 wherein $R^3CO$ is the acyl group of a NSAID.

3. The compound of claim 1 wherein the NSAID is selected from the group consisting of etodolac, tolmetin, salsalate, diflunisal and ketoprofen.

4. The compound of claim 1 wherein $R^2$ is H.

5. A pharmaceutical composition comprising a therapeutically-efective amount of a compound of any one of claims 1 to 4 and a pharmaceutically-effective carrier or diluent.

6. A pharmaceutical composition comprising a therapeutically-efective amount of a compound of any one of claims 1 to 4 and a therapeutically-effective amount of a pharmaceutical agent, wherein said agent is selected from the group consisting of a cytokine, an interleukin, an anti-cancer agent or anti-neoplastic agent, a chemotherapeutic agent, an antibody, a conjugated antibody, an immune stimulant, an antibiotic, a hormone antagonist, a growth stimulant or a combination thereof.

7. The composition of claim 6 wherein said pharmaceutical agent comprises a cytotoxic agent.

8. The composition of claim 6 wherein said antibiotic is an antiviral nucleoside antibiotic selected from the group consisting of ganciclovir, acyclovir, and famciclovir.

9. The composition of claim 6 wherein said antibiotic is ganciclovir.

10. The composition of claim 6 wherein said chemotherapeutic agent is selected from the group consisting of alkylating agents, purine and pyrimidine analogs, vinca and vinca-like alkaloids, etopside and etopside-like drugs, corticosteroids, nitrosoureas, antimetabolites, platinum based cytotoxic drugs, hormonal antagonists, anti-androgens and antiestrogens.

11. The composition of claim 6, wherein said cytokine is an interferon.

12. The composition of claim 6, wherein said immune stimulant is *Corynebactedum parvum* or a sarcolectin.

13. The composition of claim 6, wherein the chemotherapeutic agent is selected from the group consisting of tamoxifen, doxorubicin, I-asparaginase, dacarbazine, amacrine, procarbazine, hexamethylmelamine, mitoxantrone and gemcitabine.

14. The composition of claim 5 wherein said compound is α-methyl-4-(2-methylpropyl)-benzeneacetyloxymethyl butyrate, 1-{α-methyl-4(2-methylpropyl)-benzeneacetyloxy}-ethyl butyrate, 1-{α-methyl-4(2-methylpropyl)-benzeneacetyloxy}-butyl butyrate, 6-methoxy-α-methyl-2-naphthaleneacetyloxylmethyl butyrate, 1-{6-methoxy-α-methyl-2-naphthaleneacetyloxy}-ethyl butyrate or 1-{6-methoxy-α-methyl-2-naphthaleneacetyloxy}butyl butyrate.

15. The composition of claim 5 wherein the $R^3CO$ moiety of the compound is that of valproic acid or 2-valproenic acid and R is not $C_2$ to $C_{10}$ alkenyl substituted with an aryl group, $C_1$ to $C_{10}$ alkyl or hydroxy propyl.

16. A method of treating cancer or other proliferative disorder in a patient which comprises administering to the patient an amount of a compound of any one of claims 1–4 or the composition of claim 14 effective to treat the cancer or disorder.

17. The method of claim 16 wherein the disorder is leukemia, squamous cell carcinoma, prostate carcinoma, breast carcinoma, colon carcinoma, pancreatic carcinoma, lung carcinoma, renal carcinoma, neuroblastoma or melanoma.

18. The method of claim 16 wherein said compound is administered orally, parenterally, transdermally, transmucosally, intranasally, rectally or topically.

19. The method of claim 16 wherein said effective amount is an amount effective to inhibit histone deacetylase in the patient.

20. A method of differentiating or blocking proliferation of cancerous or neoplastic cells comprising administering to said cells a compound of any one of claim 1–4 or the composition of claim 14 in an amount effective to cause differentiation of or to block proliferation of said cancerous or neoplastic cells.

21. The method of claim 20 wherein the compound is administered to said cells in vivo.

22. The method of claim 20 wherein the compound is administered to said cells in vitro.

23. The method of claim 20 wherein said compound is administered orally, parenterally, transdermally, transmucosally, intranasally, rectally or topically.

24. A method of enhancing the action of a pharmaceutical agent useful for the treatment of cancer or other proliferative disorder, comprising co-administering to a patient a therapeutically-effective amount of a compound of any one of claim 1–4 or the composition of claim 14 and a therapeutically effective amount of said pharmaceutical agent, wherein said pharmaceutical agent is selected from the group consisting of a cytokine, an interleukin, an anti-cancer agent or anti-neoplastic agent, a chemotherapeutic agent, an antibody, a conjugated antibody, an immune stimulant, an antibiotic, a hormone antagonist and a growth stimulant.

25. The method of claim 24 wherein said pharmaceutical agent is an antibiotic.

26. The method of claim 25 wherein said antibiotic is an antiviral nucleoside antibiotic selected from the group consisting of ganciclovir, acyclovir, and famciclovir.

27. The method of claim 24 wherein said pharmaceutical agent is a chemotherapeutic agent.

28. The method of claim 27 wherein said chemotherapeutic agent is selected from the group consisting of an alkylating agent, a purine analog, a pyrimidine analog, a vinca alkaloid, an etoposide, a corticosteroid, a nitrosourea, an antimetabolite, a platinum-based cytotoxic drug, a hormonal antagonist, an anti-androgen and an anti-estrogen.

29. The method of claim 24 wherein said cytokine is an interferon.

30. The method of claim 27 wherein said chemotherapeutic agent is selected from the group consisting of tamoxifen, doxorubicin, 1-asparaginase, dacarbazine, amsacrine, procarbazine, hexamethylmelamine, mitoxantrone and gemcitabine.

31. The method of claim 24 wherein said pharmaceutical agent is an immune stimulant.

32. The method of claim 31 wherein said immune stimulant is *Corynebacterium parvum* or a sarcolectin.

33. The method of claim 24 wherein said compound is administered orally, parenterally, transdermally, transmucosally, intranassaly, rectally or topically.

34. A method of ameliorating the effects of a cytotoxic agent which comprises administering a therapeutically-effective amount of said cytotoxic agent and a compound of any one of claims 1–4 or the composition of claim 14 to a mammalian patient for a time and in an amount to induce growth arrest of rapidly-proliferating epithelial cells or bone marrow stem cells of said patient and thereby protecting said cells from cytotoxic effects of said agent.

35. The method of claim 34 wherein said rapidly proliferating epithelial cells are in hair follicles, gastrointestinal tract, gladder or bone marrow of said patient.

36. The method of claim 34 wherein said rapidly-proliferating epithelial cells are hair follicle cells or intestinal cryt cells of said patient.

37. The method of claim 34 wherein said compound is administered simultaneously with the cytotoxic agent.

38. The method of claim 34 wherein said cytotoxic agent is administered before or after administration of the compound.

39. The method of claim 34 wherein said compound is administered systemically or topically.

40. A method of inhibiting telomerase activity in cancer cells which comprises administering to said cells an amount of a compound of any one of claim 1–4 or the composition of claim 14 effective to decrease the basal level of telomerase activity in said cells and thereby inhibit malignant progression of said cells.

41. The method of claim 40 wherein said cells are treated in vivo.

42. The method of claim 41 wherein said compound is administered to the patient orally, parenterally, transdermally, transmucosally, intranasally, rectally or topically.

43. The method of claim 40 wherein said compound is administered to the cells in vitro.

44. A method of treating virus-associated tumors which comprises co-administering to a patient a therapeutically-effective amount of a compound of any one of claim 1–4 or the composition of claim 14 and a therapeutically-effective amount of an antiviral agent.

45. The method of claim 44 wherein said antiviral agent is ganciclovir, acyclovir, or famciclovir.

46. The method of claim 44 wherein said virus-associated tumor is an EBV-associated malignancy, Kaposi's sarcoma, an AIDS-related lymphoma, a hepatitis B-associated malignancy or a hepatitis C-associated malignancy.

47. The method of claim 44 wherein said EBV-associated malignancy is nasopharyngeal carcinoma or non-Hodgkin's lymphoma.

48. The method of claim 44 wherein said compound is administered orally, parenterally, transdermally, transmucosally, intranasally, rectally or topically.

49. A method of treating cancer or other proliferative disorder in a patient in need of such treatment which comprises administering to the patient a compound of any one of claims 1–4 or the composition of claim 14 in an amount effective to induce cellular apoptosis of the cancer cells or of the cells of the proliferative disorder.

50. The method of claim 49 wherein said compound is administered orally, parenterally, transdermally, transmucosally, intranasally, rectally or topically.

* * * * *